United States Patent [19]
Jones et al.

[11] Patent Number: 5,912,059
[45] Date of Patent: Jun. 15, 1999

[54] OSTOMY POUCH HAVING NON-TACKY FASTENER SYSTEM

[75] Inventors: Cheryl D. Jones; James J. Kobe, both of St. Paul, Minn.

[73] Assignee: Minnesota Mining and Manufacturing Company, St. Paul, Minn.

[21] Appl. No.: 08/709,241

[22] Filed: Aug. 16, 1996

[51] Int. Cl.$^6$ .............................. B32B 1/08; B29D 22/00; B29D 23/00

[52] U.S. Cl. ...................... 428/35.2; 428/35.5; 428/35.7; 428/99

[58] Field of Search ................................. 428/35.2, 35.4, 428/35.5, 35.7, 99; 604/277, 332, 337, 339, 342, 345, 408

[56] References Cited

U.S. PATENT DOCUMENTS

| | | | |
|---|---|---|---|
| 2,378,695 | 6/1945 | Fryling | 260/23 |
| 2,395,070 | 2/1946 | Sarbach | 260/36 |
| 2,535,852 | 12/1950 | Hatfield et al. | 260/27 |
| 2,648,858 | 8/1953 | Le Bolt | 128/234 |
| 2,714,562 | 8/1955 | Hechtman | 117/68.5 |
| 2,910,065 | 10/1959 | Marsan | 128/283 |
| 2,962,404 | 11/1960 | McIntyre et al. | 154/46 |
| 3,049,228 | 8/1962 | Burnett | 206/58 |
| 3,196,034 | 7/1965 | Pandolfo, III | 117/44 |
| 3,239,478 | 3/1966 | Harlan, Jr. | 260/27 |
| 3,241,795 | 3/1966 | Frye | 248/28 |
| 3,311,339 | 3/1967 | Frye | 248/205 |
| 3,574,864 | 4/1971 | Bradley | 2/114 |
| 3,635,861 | 1/1972 | Russell | 260/27 |
| 3,638,651 | 2/1972 | Torr | 128/204 |
| 3,645,835 | 2/1972 | Hodgson | 161/146 |
| 3,689,346 | 9/1972 | Rowland | 156/245 |
| 3,691,140 | 9/1972 | Silver | 260/78.5 |
| 3,745,587 | 7/1973 | Bradley | 2/114 |
| 3,849,949 | 11/1974 | Steinhauser et al. | 51/406 |
| 3,897,780 | 8/1975 | Trousil | 128/283 |
| 3,917,607 | 11/1975 | Crossland et al. | 260/28.5 |
| 3,921,221 | 11/1975 | Zoephel | 2/51 |
| 3,932,328 | 1/1976 | Korpman | 260/27 BB |
| 3,932,563 | 1/1976 | Argurio et al. | 260/897 B |
| 3,937,683 | 2/1976 | Ferrar | 260/42.47 |
| 3,954,692 | 5/1976 | Downey | 260/33.6 AQ |
| 3,985,833 | 10/1976 | Argurio et al. | 260/897 R |
| 4,018,333 | 4/1977 | Blackwood | 206/343 |
| 4,022,850 | 5/1977 | Booth et al. | 260/897 B |
| 4,040,124 | 8/1977 | Zoephel | 2/51 |
| 4,042,732 | 8/1977 | Ferrar | 427/385 R |
| 4,053,540 | 10/1977 | Argurio et al. | 260/897 B |
| 4,104,327 | 8/1978 | Inoue et al. | 260/876 B |
| 4,127,685 | 11/1978 | Busby et al. | 427/294 |

(List continued on next page.)

FOREIGN PATENT DOCUMENTS

| | | | |
|---|---|---|---|
| A 74595-87 | 1/1988 | Australia . | |
| A 11700-88 | 9/1988 | Australia . | |
| A 20442-88 | 4/1989 | Australia . | |
| 621180 | 7/1992 | Australia . | |
| 2026627 | 4/1991 | Canada . | |
| 2019283 | 9/1991 | Canada . | |
| 0 121 430 | 10/1984 | European Pat. Off. . | |
| 0 187 044 | 7/1986 | European Pat. Off. . | |
| 0 260 873 | 3/1988 | European Pat. Off. . | |
| 0 382 420 | 8/1990 | European Pat. Off. . | |
| 0 426 359 | 8/1991 | European Pat. Off. . | |
| 0 443 263 | 8/1991 | European Pat. Off. . | |
| 0 513 772 A3 | 11/1992 | European Pat. Off. . | |
| 0 611 122 A1 | 8/1994 | European Pat. Off. | A61F 5/445 |
| 0611122 | 8/1994 | European Pat. Off. . | |
| 1 918 626 | 10/1969 | Germany . | |
| A-04 180 754 | of 0000 | Japan . | |
| 62-66825 | 3/1987 | Japan . | |
| 62 112 507 | 5/1987 | Japan . | |
| 189485 | of 1988 | Japan . | |
| 118604 | 5/1989 | Japan . | |
| 138280 | 5/1989 | Japan . | |
| 2-16944 | 4/1990 | Japan . | |
| 6-136186 | 5/1994 | Japan . | |
| NI 46367 | 8/1991 | Taiwan . | |
| NI 73088 | 8/1992 | Taiwan . | |
| 1 215 796 | 12/1970 | United Kingdom . | |
| 2 116 253 | 9/1983 | United Kingdom . | |
| 2 166 427 | 5/1986 | United Kingdom . | |
| PCT/EP88/ 00176 | 9/1989 | WIPO . | |
| WO 89/11262 | 11/1989 | WIPO | A61F 13/02 |
| WP 95/10576 | 4/1995 | WIPO . | |

OTHER PUBLICATIONS

Murray, "Non–tacky reclosable tape . . ." Design News Feb. 21, 1994, pp. 85–86.
BF Goodrich Publication, "Materials for Adhesives", Mar., 1981.
Product Information, Scotchmate™ Hook and Loop Fasteners, Oct. 1989.
Technical Assoc. of the Pulp and Paper Industry, UM 213; 1991 TAPPI Useful Methods, p. 21.
*Handbook of Pressure–Sensitive Adhesive Technology*, D. Satas eds., (Van Nostrand Reinhold, NY 1982); pp. 206–209, 265–268.
*Handbook of Pressure–Sensitive Adhesive Technology*, D. Satas eds., (Van Nostrand Reinhold, NY 1989; 2nd edition); pp. 206–209, 265–268.
*Polymer Handbook*, J. Brundrup and E.H. Immergut, eds., 2, (Wiley, NY, 1975); IV–337 to IV–341.
"Non–Tacky Reclosable Tape Leaves No Residue", *Design News*, Feb. 21, 1994, pp. 85–86.
PCT Search Report for USSN 08/709,241.

*Primary Examiner*—Frank C. Eisenschenk
*Assistant Examiner*—Brett Nelson
*Attorney, Agent, or Firm*—F. Andrew Ubel

[57] ABSTRACT

A low profile, two-piece ostomy appliance is disclosed that has a contact responsive non-tacky fastener system comprising a fastener that is attached to the ostomy appliance and a landing zone component that is attached to the peristomal area of the user. The fastening layer of the fastener system is preferably multiply releasable and refastenable against the non-tacky target, and preferably has a 90° peel strength of less than about 3 kN/m and a dynamic shear strength of greater than 2 kN/m$^2$ when in contact with the target surface.

36 Claims, 6 Drawing Sheets

U.S. PATENT DOCUMENTS

| | | | |
|---|---|---|---|
| 4,136,699 | 1/1979 | Collins et al. | 128/290 R |
| 4,189,547 | 2/1980 | Osborn et al. | 525/99 |
| 4,212,912 | 7/1980 | Wartusch et al. | 428/209 |
| 4,288,567 | 9/1981 | Feeney et al. | 525/99 |
| 4,300,562 | 11/1981 | Pieniak | 128/287 |
| 4,314,558 | 2/1982 | Korpman | 128/283 |
| 4,329,384 | 5/1982 | Vesley et al. | 428/40 |
| 4,330,590 | 5/1982 | Vesley | 428/336 |
| 4,374,077 | 2/1983 | Kerfeld | 264/22 |
| 4,399,249 | 8/1983 | Bildusas | 524/271 |
| 4,414,316 | 11/1983 | Conley | 430/496 |
| 4,418,123 | 11/1983 | Bunnelle et al. | 428/517 |
| 4,420,502 | 12/1983 | Conley | 427/54.1 |
| 4,514,554 | 4/1985 | Hughes et al. | 526/339 |
| 4,522,874 | 6/1985 | Pommez | 428/284 |
| 4,558,542 | 12/1985 | Marton | 51/358 |
| 4,576,850 | 3/1986 | Martens | 428/156 |
| 4,576,854 | 3/1986 | Kurahashi | 428/204 |
| 4,584,225 | 4/1986 | Adelman | 428/71 |
| 4,643,730 | 2/1987 | Chen et al. | 604/390 |
| 4,652,491 | 3/1987 | Gobran | 428/355 |
| 4,681,574 | 7/1987 | Eastman | 604/344 |
| 4,684,685 | 8/1987 | Shuman et al. | 524/270 |
| 4,710,190 | 12/1987 | Wood et al. | 604/389 |
| 4,717,749 | 1/1988 | Tang et al. | 524/271 |
| 4,728,572 | 3/1988 | Davis | 428/355 |
| 4,759,754 | 7/1988 | Korpman | 604/387 |
| 4,761,341 | 8/1988 | Rosiak et al. | 428/512 |
| 4,778,701 | 10/1988 | Pape et al. | 428/40 |
| 4,780,367 | 10/1988 | Lau et al. | 428/355 |
| 4,785,043 | 11/1988 | Kawai et al. | 524/272 |
| 4,787,897 | 11/1988 | Torimae et al. | 604/389 |
| 4,791,024 | 12/1988 | Clerici et al. | 428/343 |
| 4,810,574 | 3/1989 | Ahner | 428/355 |
| 4,813,947 | 3/1989 | Korpman | 604/387 |
| 4,826,493 | 5/1989 | Martini et al. | 604/327 |
| 4,833,193 | 5/1989 | Sieverding | 524/486 |
| 4,861,635 | 8/1989 | Carpenter et al. | 428/40 |
| 4,871,812 | 10/1989 | Lucast et al. | 525/186 |
| 4,875,259 | 10/1989 | Appledorn | 24/576 |
| 4,887,339 | 12/1989 | Bellanger | 24/575 |
| 4,906,691 | 3/1990 | Joseph et al. | 252/99 |
| 4,942,071 | 7/1990 | Frye | 428/40 |
| 4,956,228 | 9/1990 | Clerici et al. | 428/336 |
| 4,959,265 | 9/1990 | Wood et al. | 428/343 |
| 4,973,323 | 11/1990 | Kaczmarek et al. | 604/339 |
| 4,974,384 | 12/1990 | Pacione | 52/483 |
| 4,977,003 | 12/1990 | Brown | 428/35.5 |
| 4,979,613 | 12/1990 | McLaughlin et al. | 206/233 |
| 5,006,398 | 4/1991 | Banerji | 428/220 |
| 5,019,071 | 5/1991 | Bany et al. | 604/389 |
| 5,019,072 | 5/1991 | Polski | 604/389 |
| 5,028,646 | 7/1991 | Miller et al. | 524/77 |
| 5,042,221 | 8/1991 | Pacione | 52/749 |
| 5,049,423 | 9/1991 | German, Jr. | 428/35.2 |
| 5,060,443 | 10/1991 | Pacione | 52/506 |
| 5,066,526 | 11/1991 | German, Jr. | 428/35.2 |
| 5,085,655 | 2/1992 | Mann et al. | 604/389 |
| 5,088,164 | 2/1992 | Wilson et al. | 24/576 |
| 5,112,674 | 5/1992 | German et al. | 428/216 |
| 5,112,889 | 5/1992 | Miller et al. | 524/77 |
| 5,113,555 | 5/1992 | Wilson et al. | 24/576 |
| 5,114,763 | 5/1992 | Brant et al. | 428/34.9 |
| 5,133,166 | 7/1992 | Pacione | 52/483 |
| 5,139,492 | 8/1992 | Leise, Jr. et al. | 604/339 |
| 5,141,809 | 8/1992 | Arvedson et al. | 428/349 |
| 5,141,981 | 8/1992 | George et al. | 524/417 |
| 5,144,786 | 9/1992 | Pacione | 52/747 |
| 5,145,929 | 9/1992 | Ou-Yang | 526/338 |
| 5,147,708 | 9/1992 | Brant et al. | 428/213 |
| 5,154,981 | 10/1992 | Brant et al. | 428/520 |
| 5,158,557 | 10/1992 | Noreen et al. | 604/389 |
| 5,160,770 | 11/1992 | Hoopengardner | 428/40 |
| 5,175,030 | 12/1992 | Lu et al. | 428/30 |
| 5,183,597 | 2/1993 | Lu | 264/1.4 |
| 5,196,266 | 3/1993 | Lu et al. | 428/355 |
| 5,316,849 | 5/1994 | Lu et al. | 428/355 |
| 5,423,783 | 6/1995 | Battles et al. | 604/344 |
| 5,462,782 | 10/1995 | Su | 428/40 |

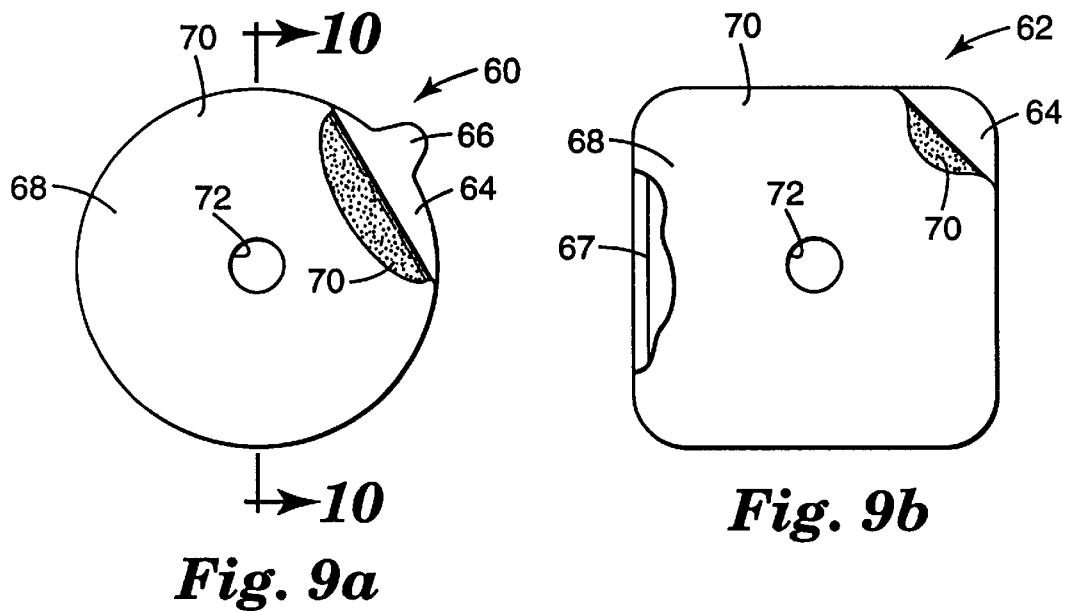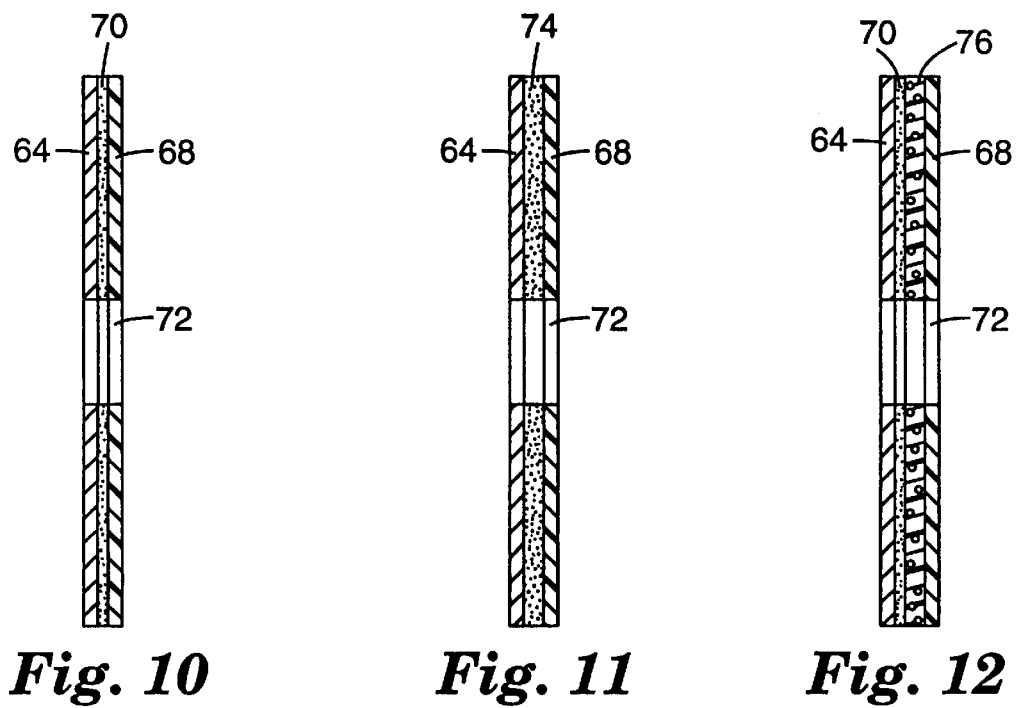

OSTOMY POUCH HAVING NON-TACKY FASTENER SYSTEM

FIELD

This invention relates to fluid collection pouches that contain non-tacky contact responsive fastener systems. In particular, the fastening systems may be incorporated into low profile, two-piece ostomy pouches and incontinence devices.

BACKGROUND

An ostomy appliance is a device used to collect waste material that exits a person's body through a stoma. The term "stoma" refers to the surgically created hole in the skin and the attached end of the bladder, conduit, or intestine. The stoma provides an open conduit through which a constant or intermittent efflux of waste material occurs. The surrounding skin area is termed the "peristomal area." A great challenge exists to comfortably and reliably connect an ostomy appliance to the peristomal area.

Sticky pressure sensitive adhesive tapes may be used for securing ostomy pouches to a patient. In one type of ostomy appliance the tapes are permanently bonded to the ostomy appliance. The ostomy appliance is used once and spent upon removal of the tape from the body.

A "two-piece" ostomy appliance may also be used. A first part is adhesively attached to the skin area around the stoma and has a snap ring of plastic that mates with a complementary snap ring on the separate ostomy device. When the two parts are snapped together, the rings form a leak-tight seal around the stoma and attach the bag to the patient. Unfortunately, however, the plastic rings are quite bulky and uncomfortable.

Other quick close/quick release mechanical fasteners are known. They may be repeatedly closed and opened and are frequently referred to as being reclosable. One such fastener, known as a hook and loop fastener, is available from Velcro U.S.A., Inc., Manchester, New Hampshire. Another such fastener, known as a mushroom-shaped fastener, is sold as the DUAL LOCK Reclosable Fastener by 3M Company, St. Paul, Minn. Both of these fasteners have certain undesirable characteristics for use in ostomy applications. For example, the hook or mushroom portions of the fasteners tend to snag fabric. Moreover, both the hook and loop portions of the fasteners tend to collect lint and dust. Also, these types of fasteners generally do not exhibit a thin profile, which may detract from an aesthetic appearance, or may not provide a liquid or odor tight seal. Another feature of the hook and loop fastener is that it makes noise when it is opened. This makes it undesirable in any application where noise is a concern.

Other known fastening systems, such as single or double sided tacky adhesive tapes also have various limitations. These limitations include non-recyclability, undesired transfer of the adhesive to a contact surface, and a tendency to irreversibly lose their adhesive properties when contaminated with lint or dust. Also, tacky adhesives tend to aggressively stick to latex surgical gloves which makes them hard to handle.

A great need exists for a reliable and inexpensive fastening system that is suitable for comfortably securing a medical device to a patient's skin.

SUMMARY

The invention provides a low profile, two-piece fluid collection pouch, such as an ostomy pouch or incontinence device, that comprises a contact responsive non-tacky fastener system. The fastener of the non-tacky fastening system comprises a non-tacky surface, and is preferably multiply releasable and refastenable against a non-tacky surface of a landing zone. The fastener may also comprise one or more layers in addition to the non-tacky surface layer such as a mounting layer of a pressure sensitive adhesive. The non-tacky surface of the landing zone may be a different material than the non-tacky surface layer of the fastener and preferably has a sufficiently different solubility parameter to prevent blocking of the two non-tacky surfaces. The target surfaces useful in the invention may generally be considered to be smooth. However, they may have some surface texture. Preferably, the target surface is essentially smooth.

A preferred contact responsive fastener system reaches its optimum and maximum peel strength relatively quickly so that a dwell time is either essentially unnecessary, or is relatively unnoticeable to a user of the fastener system. It is also desirable that the fastening system maintains a substantially constant peel strength over a long time period and does not exhibit any significant build-up of peel strength over time. A preferred contact responsive fastener system also achieves a sufficiently high shear strength to enable the fastener system to support a device. For ostomy application, the most preferred fastener system has both a suitably low peel strength, i.e., low enough that, if desired, the user easily can separate the fastener from the landing zone, and a suitably high shear strength to reliably hold the ostomy device in place.

The fastening systems of the present invention have application as a medical fastener in areas requiring conformability and where long term wear is desirable.

One specific application that this fastening system appears to be highly suited for is as a system to secure ostomy pouches to the skin. Ostomies are located on the abdomen, and therefore, require a fastener system that will preferably both conform to the abdominal contours and preferably move with the skin as the skin moves. Further, the fastener system used on ostomy pouches must be attached to the pouch film in some manner. The fastener system of the present invention can be directly sealed to typical ostomy pouch films (e.g., by heat sealing the fastener to the bag). Alternatively, an adhesive layer may be used to attach the fastener to the bag. The fastening system can be sterilized by gamma irradiation, with no loss to or only minimal effect on its properties. This feature is a highly desirable attribute of medical devices and specifically devices used to secure ostomy pouches to the peristomal region immediately after surgery.

RELATED APPLICATIONS

Of related interest to this application are the following patent applications, which are herein incorporated by reference: Ser. Nos. 08/374,133 (filed Jan. 18, 1995); 08/455,174 (filed May 31, 1995); 08/454,749 (filed May 31, 1995); 08/204,007 (filed Mar. 1, 1994); 08/035,387 (filed Mar. 22, 1993); 07/981,019 (filed Nov. 24, 1992); 07/573,321 (filed Aug. 29, 1990); and 07/427,448 (filed Oct. 26, 1989).

BRIEF DESCRIPTION OF THE DRAWINGS

This invention will be better understood when taken in conjunction with the drawings wherein:

FIGS. 9a and 9b are alternative top views of landing zones of the present invention, illustrating a non-tacky surface for the fastening system, and the adhesive layer used to attached the landing zone to a patient;

FIG. 10 is a cross-section view of the landing zone of FIG. 9a, taken along line 10—10, illustrating a non-tacky surface layer, the pressure sensitive adhesive layer used to attach the landing zone to a patient, and the liner used to protect and cover the pressure sensitive adhesive prior to use;

FIGS. 11 and 12 illustrate alternative cross-section views of the landing zone of the present invention illustrating various layers of the landing zones depicted;

Figure 1:
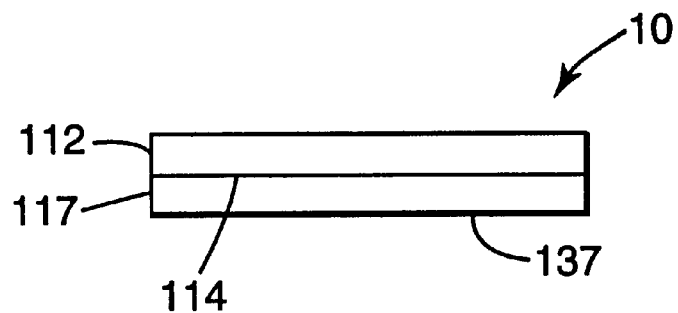
FIG. 1 is a side view of a fastener of the fastening system.

This invention utilizes certain principles and/or concepts as are set forth in the claims appended to this specification. Those skilled in the art to which this invention pertains will realize that these principles and/or concepts are capable of being illustrated in a variety of embodiments which may differ from the exact embodiments utilized for illustrative purposes in this specification. For these reasons, the invention described in this specification is not to be construed as being limited to only the illustrative embodiments but is only to be construed in view of the appended claims.

DEFINITIONS

Unless otherwise specified, the terms "fastening system" or "fastener system" in this specification refers to the combination of a fastener and a landing zone.

A "fastener" refers to that part of the fastening system of an ostomy appliance that is associated with the ostomy bag. The fastener includes a non-tacky surface and any optional mounting layers, backings, or liners that are associated with the non-tacky surface.

A "fastening component" refers to that part of the fastener that includes the non-tacky surface layer and any optional backing that is attached to the non-tacky surface layer. This does not include any mounting layer (e.g., a tacky pressure sensitive adhesive layer) or any removable liners.

A "landing zone" refers to that part of the fastening system of an ostomy appliance that is meant to be attached to the peristomal region of a user. The landing zone includes a non-tacky surface and any optional mounting layers (e.g., a tacky pressure sensitive adhesive layer), backings or liners that are associated with the non-tacky surface.

A "fastening layer" refers to the contact responsive non-tacky layer of the fastening system that is placed in contact with a target surface.

A "target surface" refers to the non-tacky layer of the fastening system that is placed in contact with a fastening layer.

DETAILED DESCRIPTION

The invention relates to a novel low profile, two-piece fluid collection pouch (e.g., a two-piece ostomy pouch) having a new class of fastening system that has at least one contact responsive fastening layer which has essentially no surface tack to paper or skin. The contact responsive fastening layer preferably allows multiple fastening and releasing cycles of the fastening layer with a target surface. The target surface may comprise either another essentially tack free surface or it may simply be a non-tacky smooth surface. The target surface preferably has a solubility parameter or other characteristic (such as surface roughness) which permits maximum contact area with the fastening layer and which allows the fastening layer to have a selectable and consistently repeatable low peel strength and a high shear strength. Preferably, the fastening layer may be cycled against the target surface numerous times without any noticeable transfer or migration of any part of either the fastening layer to the target surface or the target surface to the fastening layer. A presently preferred fastening system of the present invention for use on ostomy appliances is a low profile fastening system that has a total combined thickness (including any adhesive layers used to attach the system to a patient, but not including any removable liners that protect the system prior to use) of no more than about 0.3 mm.

Either piece of the two-piece fluid collection pouch may comprise the fastening layer. The other piece may comprise the target surface. For example, the fastening layer may be attached to or a part of the ostomy bag, and a target surface layer may be attached to or a part of the landing zone. Alternatively, the ostomy bag may comprise a target surface around the opening and the landing zone may comprise a fastening layer.

Numerous polymeric materials may be used as the contact responsive fastening layer. The polymeric material may be a homopolymer, a random copolymer, a block copolymer, or a graft copolymer. It may be crosslinked or uncrosslinked. Specific examples of polymers useful as the fastening layer include ethylene-containing copolymers, urethane polymers such as urethanes prepared by the reaction of an isocyanate and an isocyanate-reactive compound, acrylic and acrylate polymers, urethane-acrylate polymers, butyl rubber, butadiene-acrylonitrile polymers, and butadieneacrylonitrile-isoprene polymers. Blends and mixtures of polymeric materials may be used if desired.

Various other materials may be incorporated into the polymeric material. For example, tackifiers may be used if desired. Additionally, fillers, pigment, plasticizers, antioxidants, ultraviolet light stabilizers, and so forth may be employed. The exact quantity of these other materials may be varied to suit the desires of the compounder, provided that the resulting contact responsive layer retains its essentially tack-free character. Thus, the ratio of the various other materials (i.e., tackifier, filler, and/or pigment) may be varied as needed to maintain the tack-free nature of the contact responsive layer.

Additional discussion regarding polymers and compositions useful as the fastening layer may be found in a number of publications. For example, European Patent Pub. No. EP 0443263 (Miller et al.) discloses tackified block copolymer materials; U.S. Pat. No. 5,196,266 (Lu et al.) discloses urethaneacrylate materials; and U.S. Pat. Nos. 5,114,763, 5,141,809, 5,141,981 and 5,147,708, each disclose polyethylene-containing polymers with tackifiers, ethylene-vinyl acetate and acrylates. These patents are incorporated herein by reference with respect to the polymers and compositions.

Preferred polymers for use as the contact responsive fastening layer are selected from the group consisting of butadiene-acrylonitrile (hereinafter BACN) polymers, butadiene-acrylonitrile-isoprene (hereinafter BACNI) polymers, urethane acrylate (hereinafter UA) polymers, butyl rubber polymers, two-part urethane (hereinafter UR) polymers, styrene-isoprene-styrene (hereinafter SIS) block copolymers and styrene-butadiene-styrene (hereinafter SBS) polymers. BACN, BACNI, and UA polymers are presently most preferred for use as the contact responsive fastening layer.

The BACN and BACNI polymers typically have from 10 to 50% by weight acrylonitrile units. Additionally, the BACNI polymer typically contains from 2 to 20% by weight isoprene units. Either of these types of polymer may be processed by solvent coating or hot melt extrusion. Hot melt extrusion is preferred because it obviates the necessity to use solvents during processing; it provides an ability to coat the fastening layer directly onto cloth or porous backings; it is a low cost process and uses low cost materials; and it is not necessary to add a crosslinker to further crosslink the composition, since hot melt extrusion of butadiene-containing materials is known to cause some chemical crosslinking. The result is an essentially tack free hot melt coated contact responsive fastening layer with all of the above features as well as most of the desirable features of hook and loop fastening systems.

The UA polymer is primarily designed for adhesion to itself but it also works very well with a variety of target surfaces. This polymer comprises (i) a one-part, preferably solvent-free, radiation-curable, addition-polymerizable, crosslinkable, organic oligomeric resin having one or more like or different hard segments, one or more like or different soft segments, and one or more like or different monovalent moieties containing a radiation-sensitive, additionpolymerizable, functional group, and (ii) a photo-initiator.

The butyl rubber polymers are preferably combined with a de-tackifying agent, such as talc, to decrease the tack of these compositions depending upon the target surface.

While the precise nature of the contact responsive layer may be varied to suit the particular application, it should be noted that for multiply releasable and refastenable applications the preferred layer does not block, i.e., form a permanent bond to a target surface. Preferably, the contact responsive fastening layer demonstrates 90° peel strength values to a target surface of about 0.01 kN/m to about 3 kN/m, more preferably within a range of about 0.05 kN/m to about 1.5 kN/m, most preferably within a range of about 0.1 kN/m to about 1 kN/m, and optimally within a range of about 0.2 kN/m to about 0.5 kN/m. Preferably, the contact responsive fastening layer demonstrates 180° peel strength values to a target surface of about 0.005 kN/m to about 3 kN/m, more preferably within a range of about 0.01 kN/m to about 1.5 kN/m, and most preferably within a range of about 0.01 kN/m to about 0.5 kN/m. Preferably, the contact responsive fastening layer demonstrates dynamic shear strength values to a target surface of greater than about 2 $kN/m^2$ more preferably greater than about 4 $kN/m^2$, and most preferably greater than 6 $kN/m^2$. Preferably, the contact responsive fastening layer demonstrates static shear strength ("holding power") values to a target surface of greater than about 60 minutes, more preferably greater than about 500 minutes, most preferably greater than about 1100 minutes, and optimally greater than about 1700 minutes. These strength values are measured according to the techniques described hereinafter. For purposes of comparison, peel strength and dynamic shear strength values are measured after about 10 minutes dwell at 21° C.

In some cases, it may be necessary to adjust the coating weight/coating thickness to achieve the desired peel value. Furthermore, the polymer may be additionally crosslinked in order to further increase its internal strength and reduce peel values to a desired level. This is an especially useful technique to use when the contact responsive layer and the target surface comprises BACN, BACNI, or a combination of each. In this instance, the BACN and/or BACNI polymer is preferably modified by crosslinking in order to prevent blocking of the contact responsive layer to the target surface. Crosslinking is one method for increasing the internal strength of the BACN so that the fastening layer maintains a relatively constant peel strength over repeated uses. Additionally, crosslinking provides a means for controlling the peel strength of the material against another material.

The adhesive properties of the fastener system of the invention can also be controlled by appropriate selection of the target surface to which it is to be fastened. It has been discovered that for some fastener systems, particularly a BACN system, as the difference between solubility parameter of the fastening layer and that of the target surface increases, the peel strength (e.g., as exemplified by 180° peel strength) decreases.

Target surfaces useful in the invention may be selected from a wide variety of materials. Especially useful target surfaces are materials that do not bond permanently to the fastening layer. Examples of useful target surfaces include those materials previously identified as being useful for the fastening layer, as well as polyurethanes, polycarbonate, polyacrylonitrile, butadienestyrene polymers, poly (methylmethacrylate), polyamide, ethylene vinylacetate copolymer, treated and untreated poly(ethylene terephthalate), olefinic ionomer resins such as "SURLYN" resins from E.I. Du Pont de Nemours and Company, Wilmington, Del., polystyrene, acrylonitrile butadiene-styrene polymer, polypropylene, and polyethylene. Useful target surfaces may also include metallic surfaces such as foils; coated paper; enamel coated substrates; low adhesive backsize coatings (LABs); paints; inks; lacquers; etc. The exact choice of target surface to be used is dependent upon the needs of the user, provided however, that the target surface and fastening layer do not block.

It has also been discovered that the peel strength can be influenced by the nature of any mounting layer that may be used. For example, higher peel values are typically obtained when a stiff (i.e., rigid) mounting layer is utilized.

An advantageous feature of this fastening system is that it is cleanable, for example, with isopropanol or soap and water, in order to maintain/restore its fastening characteristics. This is a valuable consideration in view of the tendency of these compositions to eventually lose fastening capability when contacted with certain contaminants, such as oils. However, the rejuvenation of these fastener systems results in a long useful life of products using these systems.

If desired, the fastening component of the present invention may comprise on the surface opposite the non-tacky surface layer a mounting layer such as a material capable of heat or sonic bonding. This enables the fastener to be directly heat bonded to a structure such as a plastic film of an ostomy bag. Alternatively, the fastener may be directly laminated to the article or adhered to the article using a layer of a tacky pressure sensitive adhesive.

The fastener and/or the landing zone can be coated with any conventional hot melt, solvent coated, or like adhesive. These adhesives can be applied by conventional techniques, such as solvent coating by methods such as reverse roll, knife-over-roll, gravure, wire wound rod, floating knife or air knife, hot-melt coating such as by slot orifice coaters, roll coaters or extrusion coaters, at appropriate coating weights. U.S. Pat. No. 5,230,701 (Meyer et al.), which is herein incorporated by reference, discloses suitable adhesive coating methods. The adhesive may be first coated on a liner material, using one of the aforementioned techniques, and then laminated (e.g., using a roller to apply pressure) to form the fastener or landing zone. Preferred for most applications would be pressure sensitive adhesives. Suitable pressure sensitive adhesives for use in the present invention include those pressure sensitive adhesives which are capable of providing the necessary amount of peel strength and/or shear strength to function in the manner required (e.g., sufficient shear strength to securely attach the ostomy appliance to the skin without unintended detachment). Suitable adhesives for use in the medical field should be non-toxic, preferably hypoallergenic, and are most preferably also environmentally safe.

Suitable pressure sensitive acrylate adhesives for use in the present invention, e.g., for use on the skin contacting surface of the landing zone component, include copolymers which are reaction products of the polymerization of at least one "A" monomer and at least one "B" monomer to yield a copolymer preferably having an inherent viscosity of about 1.0 dl/g to about 2.0 dl/g. The A monomer is a polymerizable monomer comprising an acrylate or methacrylate ester of a non-tertiary alcohol or a mixture of non-tertiary alcohols with the alcohols having from about 1 to 14 carbon atoms and desirably averaging about 4 to 12 carbon atoms. The B monomer is an ethylenically unsaturated compound and desirably may be acrylic acid, methacrylic acid, itaconic acid, acrylamide, methacrylamide, acrylonitrile, methacrylonitrile, vinyl acetate, N-vinyl pyrrolidone, or combinations thereof. The A monomer is polymerizable and contributes the viscoelastic properties of the pressure sensitive adhesive copolymer. Non-limiting examples of such A monomers include the esters of acrylic acid or methacrylic acid with non-tertiary alkyl alcohol such as 1-butanol, 1-pentanol, 2-pentanol, 3-pentanol, 2-methyl-1 butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like. Such monomeric acrylic or methacrylic esters are known in the art, and many are commercially available. The B monomer is an ethylenically unsaturated compound copolymerized with the A monomer to affect the physical properties of the resulting pressure sensitive adhesive copolymer. In general, the presence of the B monomer will reduce the flexibility of the resulting pressure sensitive adhesive copolymer. Thus, the weight percentages of the A monomer and the B monomer should be balanced in order to provide a pressure sensitive adhesive copolymer preferably having an inherent viscosity of from about 1.0 dl/g to about 2.0 dl/g. The weight percentage ratio of A monomer: B monomer ranges from about 85:15 to about 98:2 and desirably from about 90:10 to 97:3.

The pressure sensitive adhesive copolymer should be tacky at room temperature as well as at skin temperature of mammals. Also, the adhesive should be hypoallergenic, i.e., after continuous contact with skin, there is no significant skin sensitization or irritation during adhesion. Presently preferred as an acrylate pressure sensitive adhesive for tapes used in the present invention is an isooctyl acrylate/acrylic acid copolymer in a weight ratio of about 94:6. The inherent viscosity of the copolymer is about 1.4–1.6 dl/g. If desired, acrylate pressure sensitive adhesives have a tackifier added to the formulation to improve tack. Commercially available tackifiers include "Foral" branded colophony acid rosins, such as "Foral AX" and "Foral 85" rosins, commercially available from Hercules Corporation, and partially hydrogenated methylstyrene hydrocarbon resins, such as "Piccolastic A25" resin, also commercially available from Hercules Corporation. Such tackifiers can be added during preparation of the acrylate pressure sensitive adhesive in an amount of about 35–40 weight percent of the copolymer solids.

Alternate pressure sensitive adhesives useful in the present invention are hypoallergenic Kraton rubber-based pressure sensitive adhesives produced using styrene-butadiene or styrene-isoprene copolymers commercially available as Kraton branded copolymers from Shell Oil Company of Houston, Tex. A variety of Kraton based pressure sensitive adhesives are disclosed in U.S. Pat. Nos. 5,019,071 (Bany et al.) and 5,158,557 (Noreen et al.), the disclosures of which are incorporated by reference herein. Preferred as Kraton rubber-based pressure sensitive adhesives are Kraton 1107, Kraton 1111, Kraton 1101, and Kraton D branded copolymers, tackified with compatible tackifiers such as Escorez ™ 1310LC branded tackifier commercially available from Exxon Chemicals, a solid $C_5$ tackifying resin commercially available as Wingtack™ Plus brand tackifier from Goodyear Tire and Rubber Company, Akron, Ohio and naphthenic oils having 10% aromatics commercially available as Shellflex™ 371 from Shell Oil Company. Such tackifiers can comprise about 45 to about 70 weight percent of the pressure sensitive adhesive, while the Kraton copolymer can comprise about 30 to 55 weight percent.

Additional alternate pressure sensitive adhesives which may be useful in the present invention are the water-dispersible pressure sensitive adhesives disclosed in U.S. Pat. Nos. 3,865,770; 4,413,080; 4,569,960; 5,125,995; 5,270,111; and 5,397,614 and in U.S. patent application Ser. Nos. 07/763,823; and 07/889,647; the disclosures of which are herein incorporated by reference.

Pressure sensitive adhesive copolymers can be copolymerized using known polymerization techniques such as emulsion polymerization and solution polymerization. Sources of polymerization preparation and techniques include *Organic Polymer Chemistry*, Saunders et al. (Halsted Publishing Company, New York 1973); *Applied Polymer Science*, Tess et al. (American Chemical Society, Washington, D.C., 1981); *Principles of Polymerization*, Odien (John Wiley and Sons, New York, 1981); and the *Handbook of Pressure-Sensitive Adhesive Technology, Second Edition*, Satas, Ed., (Van Nostrand Reinhold Company, New York, 1989), the disclosures of which are incorporated by reference. Specifically, acrylate pressure sensitive adhesive copolymers can be prepared according to U.S. Pat. No. 2,884,126/RE 24,906 (Ulrich), the disclosure of which is incorporated by reference herein.

DETAILED DESCRIPTION OF THE DRAWINGS

A number of specific embodiments of the invention are illustrated in the Figures.

FIG. 1 discloses multilayered tape 10 comprising contact responsive fastening layer 112 having a first surface 114 attached to an optional mounting layer 117. Mounting layer 117 preferably comprises a tacky pressure sensitive adhesive. Mounting layer 117 permits permanent mounting of tape 10 to another substrate in a position which enables multiple releasable contact between fastening layer 112 and a target surface. When the composition of fastening layer 112 is a urethane-acrylate polymer, it may be coated directly onto mounting layer 117 and cured with ultraviolet radiation. Alternately, when the composition of fastening layer 112 is a butadiene-acrylonitrile polymer or a butadieneacrylonitrile-isoprene polymer, it may be hot melt or solvent coated onto mounting layer 117. In either embodiment, as with other suitable compositions, a novel multilayered tape 10 results. Fastening layer 112 may also be mounted directly to certain substrates without using a mounting layer comprising a pressure sensitive adhesive. For example, fastening layer 112 may adhere directly to the substrate. Provided that the adhesion to the substrate is greater than the adhesion to the target surface, the fastening layer will remain attached to the substrate. Alternatively, the mounting layer 117 may comprise a layer of material that can be heat sealed to a substrate. For example, mounting layer 117 may comprise a polymeric film.

Figure 2:
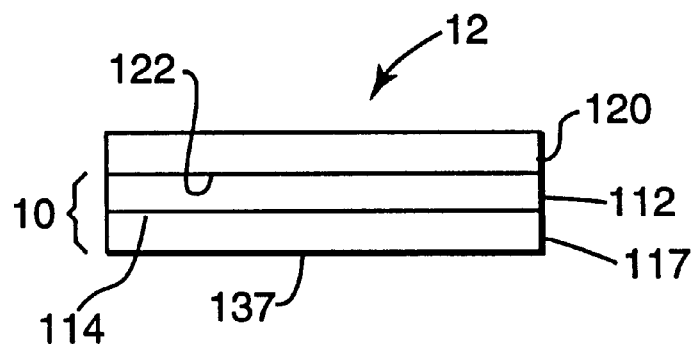
FIG. 2 is a side view of a fastener of the fastening system with a removable cover layer.

FIG. 2 illustrates the tape of FIG. 1 having an additional layer of material. In this embodiment, a covering layer 120, such as a removable liner, is attached to a second surface 122 of the fastening layer 112. After tape 12 is properly positioned, and optional mounting layer 117 is firmly attached to the underlying substrate, the covering layer may be removed to allow placement of a target surface against fastening layer 112. This sequence permits ease of placement of tape 12 without contaminating fastening layer 112.

Figure 3:
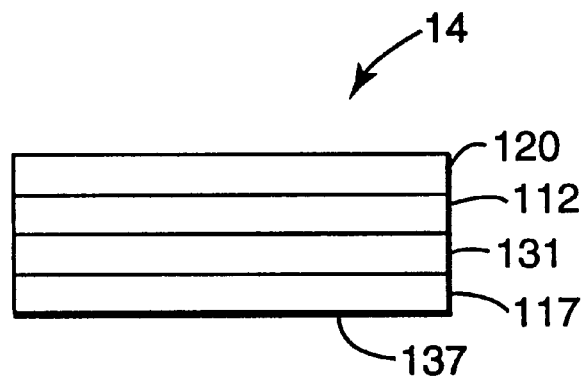
FIG. 3 is a side view of a fastener of the fastening system with an interposing backing layer.

FIG. 3 illustrates yet a further alternative tape 14. This tape is similar in use and structure to tape 12, but has an additional backing layer 131. Backing layer 131 may comprise a scrim, a woven material, a non-woven material, paper, metal foil, or a polymeric material, such as a film. Other materials may also be used as backing layer 131 provided there is the desired level of adhesion to and material compatibility with both fastening layer 112 and mounting layer 117. Specific types of materials that are useful as the backing material 131 include polycarbonate, poly(methylmethacrylate), polypropylene, polyethylene, polystyrene, acrylonitrile-butadiene styrene polymer, and polyester. Other useful materials for backing layer 131 include oriented poly(ethylene terephthalate) film with or without a corona treated surface, cellulose acetate butyrate, cellulose acetate propionate, poly(ether sulfone), polyurethane, poly(vinyl chloride), paper, fabric and metal. The presently most preferred backing material is a polyester film which preferably has been corona treated.

Backing layer 131 should be of a thickness to provide sufficient support to fastening layer 112. Backing layer 131 is preferably at least 0.0125 mm thick, in order to provide both good strength and good handling properties to the tape. It is preferred that the substrate comprising backing layer 131 have a tensile strength of at least about 1500 MPa. In many applications it is also preferred that the backing layer be flexible, i.e., capable of being bent to a radius of 0.5 cm without breaking.

The embodiment of FIG. 3 may be mounted directly to the substrate without the need for mounting layer 117. In FIGS. 1–3, an optional removable liner may be attached to an exposed second surface 137 of mounting layer 117. Use of these tapes with appropriate liners permit bulk roll storage and dispensing and provide ease of manufacture of articles using the tape.

Figure 4:
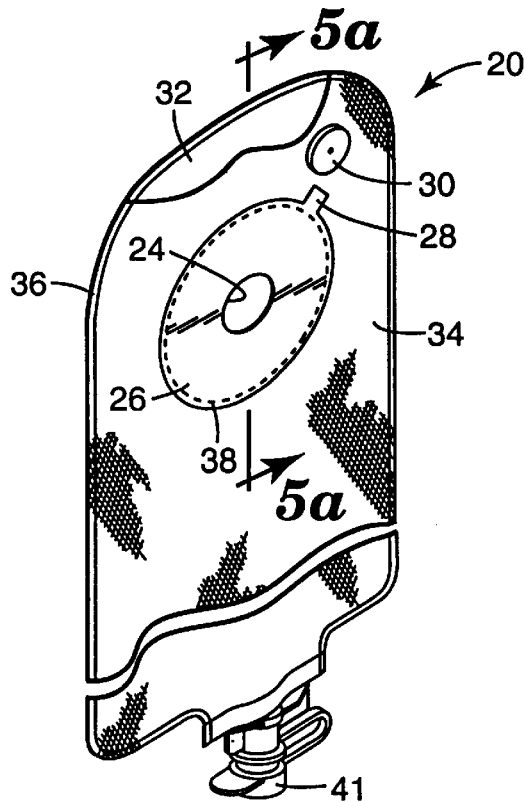
FIG. 4 is an perspective view of an ostomy pouch having a non-tacky fastener system.

FIG. 4 illustrates a perspective view of an ostomy appliance (or "ostomy bag") 20 having a non-tacky fastener 26. The ostomy pouch 20 is formed from two layers of a fluid impermeable material 32 such as a plastic film. The bag optionally has a layer of a comfort material 34 such as a non-woven fabric on the patient side of the bag. The layers of fluid impermeable material and optional comfort layer 34 may be sealed at edge 36 using, for example, an adhesive or a heat sealing technique to form the pouch. Also shown in FIG. 4 are an optional drain 41 and an optional odor vent 30. Fastener 26 optionally and preferably has a non-adherent tab 28 to facilitate removal of the fastener system from a landing zone (e.g., by peeling). FIG. 4 further illustrates an opening 24 into the pouch. If desired, the opening can be either pre-sized for a particular patient's need (i.e., the pouch may be manufactured with a variety of opening sizes) or may be a universal "starter" opening that is then enlarged by the user to fit their particular need. The fastener 26 may be attached to the ostomy bag in a variety of ways. As shown in FIG. 4, the fastener is attached to the bag from near the opening 24 to near the periphery of the fastener 26. In one preferred embodiment, the attachment is achieved by heat sealing 38 the fastener 26 to the bag material 32. This may be accomplished using any of a variety of heat sealing patterns, such as, for example, a series of circular lines of different diameters.

Figure 5A:
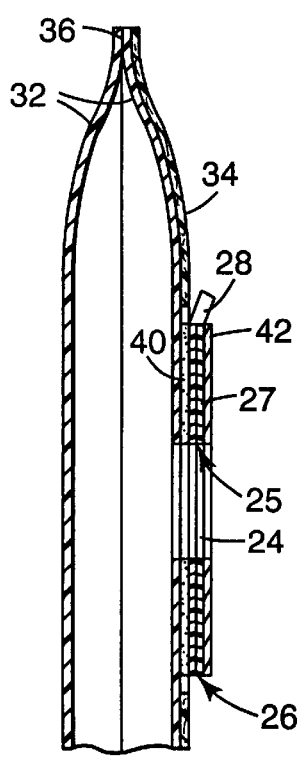
FIG. 5a is a partial cross-section view of the pouch of FIG. 4, taken along line 5a–5a, showing the fastening component of the fastening system, an adhesive layer that attaches the fastening component to the ostomy bag, and an optional liner that covers and protects the non-tacky surface layer of the fastening component.

FIG. 5a illustrates a partial cross-section view of the pouch of FIG. 4, taken along line 5a–5a, showing the fastening component 25 of the fastener 26, an adhesive layer 40 that attaches the fastening component 25 to the ostomy bag film 32, and a liner 42 that covers and protects the non-tacky surface layer 27 (e.g., a fastening layer) of the fastening component 25. FIG. 5a also illustrates optional comfort layer 34, optional tab 28, and opening 24. If desired, tab 28 may either be a separate piece of material that is attached, e.g., by gluing, to the fastening component, or it may be an integral portion of the fastening component. In one embodiment, the fastener 26 is die cut to form both the generally circular periphery of the fastener and the finger sized tab. The tab portion of the die cut material may be coated or treated to inhibit its adhesion to the landing zone, or it may be covered with a second layer to prevent adhesion to the landing zone.

Figure 5B:
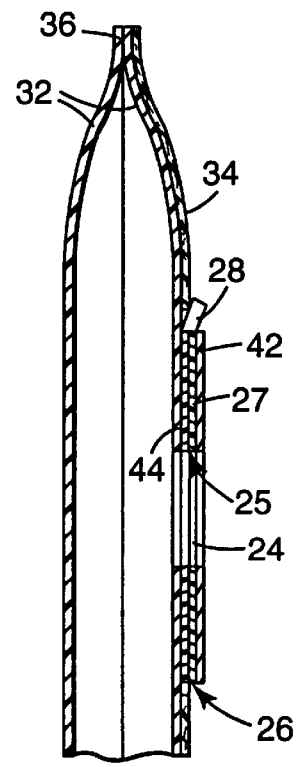
FIGS. 5b to 5f are alternative partial cross-section views of the ostomy pouch of the present invention illustrating various layers of the fastener.

FIG. 5b is an alternative partial cross-section view of the ostomy pouch 20 of the present invention illustrating various layers of the fastener 26. In this embodiment, the fastener 26 is attached to the ostomy pouch by heat sealing 44 the fastening component to the pouch film material 32.

Figure 5C:
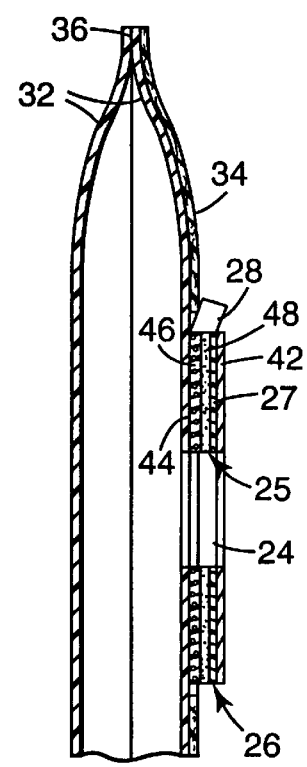

FIG. 5c is an alternative partial cross-section view of the ostomy pouch 20 of the present invention illustrating various layers of the fastener 26. In this embodiment, the fastener comprises a gap filling material 46, such as a foam, between the bag and the fastening component 25. The fastening component 25 may be adhered to the gap filling material by means of adhesive layer 48. The gap filling material may be attached to pouch film material 32 by means of an adhesive layer (not shown) or by other means such as by heat sealing 44. A removable liner 42 may be used to protect the fastener.

Figure 5D:
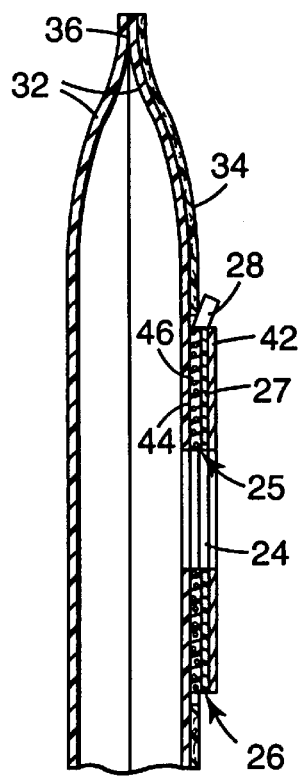

FIG. 5d illustrates a similar fastener to that shown in FIG. 5c, except that non-tacky surface layer 27 is shown directly laminated to gap filling material 46. For example, gap filling material 46 may comprise a polymeric foam material or a foamed pressure sensitive adhesive.

Figure 5E:
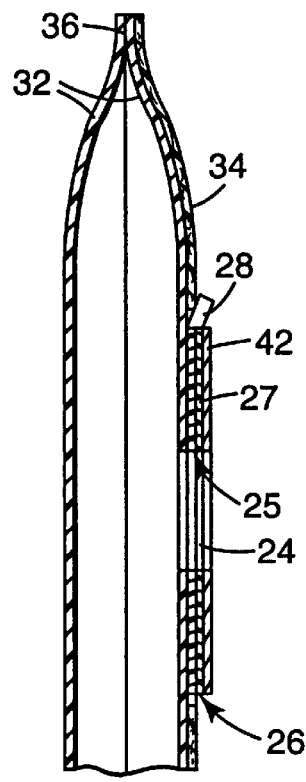

FIG. 5e illustrates a similar fastener to that shown in FIG. 5b, except that fastening component 25 is shown directly laminated to bag film 32. Fastening component 25 may comprise, for example, a non-tacky surface layer 27 and a backing (as shown) or a single layer of a non-tacky surface layer 27. For example, the fastening component 25 may comprise a single layer of a fastening layer that is directly heat sealed or otherwise laminated to the bag.

Figure 5F:
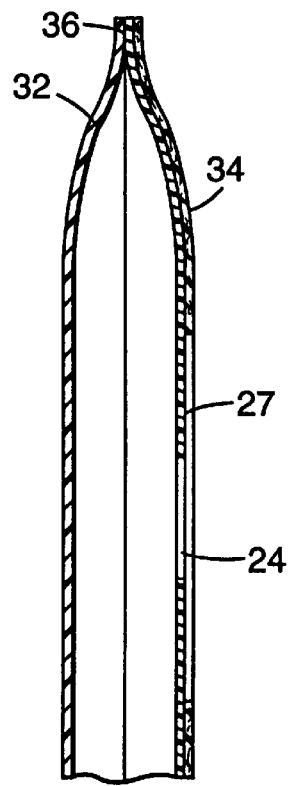

FIG. 5f illustrates an alternative partial side view of an ostomy pouch illustrating various layers of the pouch. In this embodiment, the fastener comprises the non-tacky surface 27 of the bag film near the opening 24. Optional comfort layer 34 is provided on the patient side of the pouch and away from the fastener area.

Figure 6:
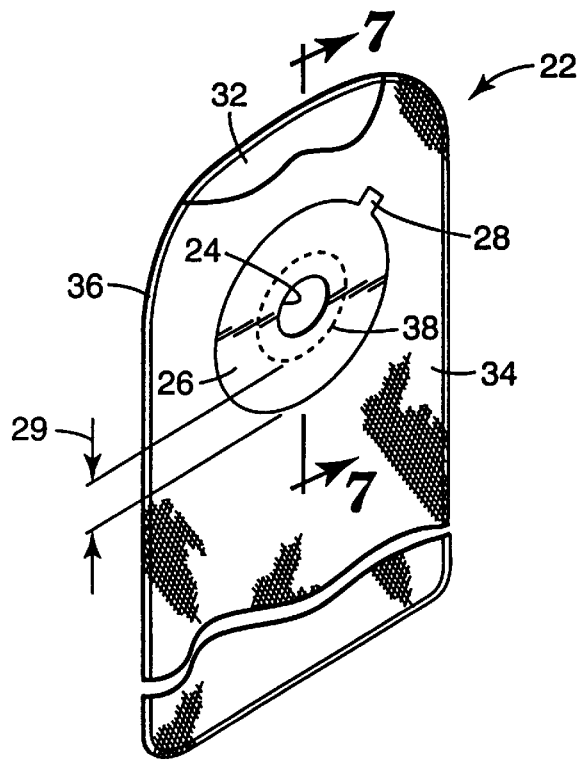
FIG. 6 is an perspective view of an alternative ostomy pouch having a non-tacky fastener system, wherein the fastener system is attached to the ostomy pouch so as to form a flange.

FIG. 6 illustrates a perspective view of an alternative ostomy pouch (or "ostomy bag") 22 having a non-tacky fastener 26. The fastener 26 of this embodiment is partially attached to the ostomy pouch 22 so as to form a flange 29. The ostomy pouch 22 is formed from two layers of a fluid impermeable material 32 such as a plastic film. The bag optionally has a layer of a comfort material 34 such as a non-woven fabric on the patient side of the bag. The layers of fluid impermeable material and optional comfort layer 34 are sealed at edge 36 using an adhesive or a heat sealing technique to form the pouch. Fastener 26 optionally and preferably has a non-adherent tab 28 to facilitate removal of the fastener (e.g., by peeling) from the landing zone. FIG. 6 further illustrates an opening 24 into the pouch. The fastener 26 may be attached to the ostomy bag in a variety of ways. As shown in FIG. 6, the fastener is attached to the bag from near the opening 24 to midway to the periphery of the fastener 26. Preferably, the attachment is achieved by heat sealing 38 the central portion of the fastener is 26 to the bag material 32. This may be accomplished using any of a variety of heat sealing patterns, such as, for example, a series of circular lines of different diameters. The peripheral portion of the fastener not connected to the bag forms a flange 29. The flange 29 is designed to relieve stress when the bag is tugged. Essentially, the flange 29 transmits tugging forces from the bag to the midpoint of the fastener. This helps relieve stresses at the periphery that might otherwise start a peeling delamination of the fastener from the landing zone. Instead, the tugging forces are distributed over a larger area of the fastening system.

Figure 7:
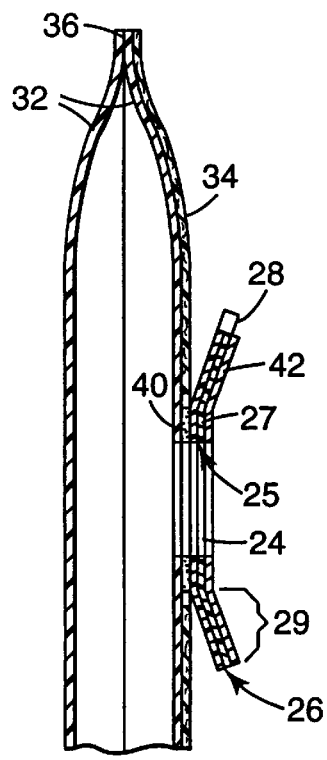
FIG. 7 is a partial cross-section view of the pouch of FIG. 6, taken along line 7—7, showing the fastening component of the fastening system, an adhesive layer that partially attaches the fastening component to the ostomy bag and that forms a flange, and an optional liner that covers and protects the non-tacky surface layer of the fastening component.

FIG. 7 illustrates a partial cross-section view of the pouch of FIG. 6, taken along line 7—7, showing the fastening component 25 of the fastener 26, an adhesive layer 40 that attaches a central portion of the fastening component 25 to the ostomy bag film 32, and a liner 42 that covers and protects the non-tacky surface 27 of the fastening component 25. FIG. 7 further illustrates flange 29.

Figure 8:
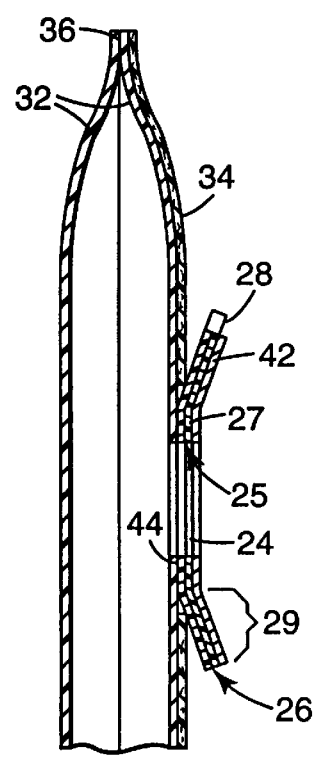
FIG. 8 is an alternative partial cross-section view of the ostomy pouch of the present invention illustrating various layers of the flanged fastener.

FIG. 8 is an alternative partial cross-section view of the ostomy pouch 22 of the present invention illustrating various layers of the flanged fastener 26. In this embodiment, the fastener 26 is attached to the ostomy pouch by heat sealing 44 the center portion of the fastening component to the pouch.

FIGS. 9a and 9b are alternative top views of landing zones (60, 62) of the present invention, illustrating a non-tacky surface 68, and the adhesive layer 70 used to attached the landing zone 60 to a patient. As shown in FIG. 9a, the landing zone 60 has a central hole 72 and optional tab 66 for separating a releasable liner 64 from the tacky skin adhesive layer 70. Alternatively, and as shown in FIG. 9b, the liner 64 may be slit 67. A first piece of liner may be removed by bending the liner at the slit. If desired, the landing zone (60, 62) may be formed using a commercial medical tape material (e.g., TEGADERM, available from 3M, St. Paul, Minn.) or another material as described herein. The precise shape of the landing zone is not critical. Preferably the landing zone is sized to mate with the fastener. The shape of the landing zone and/or fastener may be purposely mismatched, if desired, to create non-adhered regions that facilitate peeling apart of the components by the user.

FIG. 10 is a cross-section view of the landing zone of FIG. 9a, taken along line 10—10, illustrating the non-tacky surface layer 68, the pressure sensitive adhesive layer 70 used to attach the landing zone to a patient, and the liner 64 used to protect and cover the pressure sensitive adhesive prior to use. If desired, the liner material may optionally be slit in two or more pieces, thus facilitating removal (e.g., by peeling) and/or also facilitating application to the skin (e.g., wherein a portion of the liner material is first removed to expose adhesive and a second portion of the liner functions as a stiffening ring which is removed after the exposed portion of the attachment means is pressed against the skin).

FIGS. 11 and 12 illustrate alternative cross-section views of the landing zone of the present invention illustrating various layers of the landing zones depicted. In FIG. 11, the landing zone comprises a thick skin barrier adhesive 74. An example of such an adhesive is a hydrocolloid adhesive. FIG. 12 illustrates a landing zone that has a thick foam material 76 between non-tacky surface layer 68 and adhesive layer 70. Foam material 76 and/or skin barrier adhesive 74 of FIG. 11 may be used to provide a "gap filling" function. These somewhat thicker layers may help to ensure a tight leak-free seal of the bag to the user.

Figure 13:
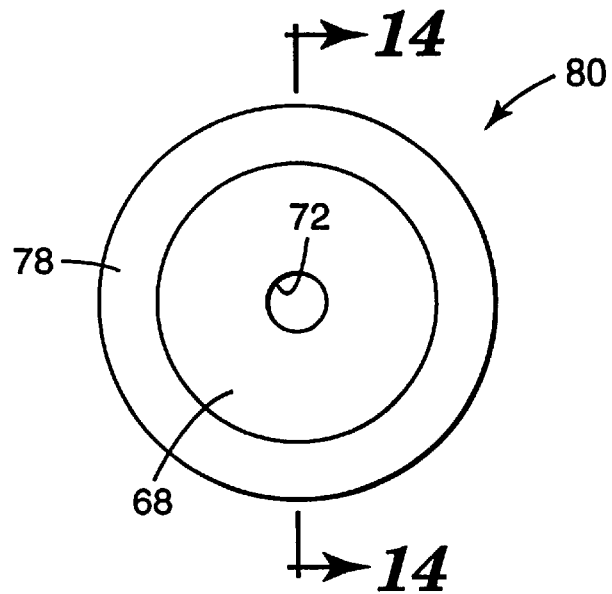
FIG. 13 is an top view of an alternative landing zone of the present invention, illustrating a non-tacky surface for the fastening system, the adhesive layer used to attach the landing zone to a patient, and an adhesive collar that surrounds the non-tacky surface and that further helps to hold the landing zone to the patient.

FIG. 13 is a top view of an alternative landing zone 80 of the present invention, illustrating the non-tacky surface layer 68 for the fastening system, and a collar tape 78 that surrounds the non-tacky surface layer and that helps to hold the landing zone to the patient. An adhesive layer under the central portion of the landing zone is illustrated in FIG. 14.

Figure 14:
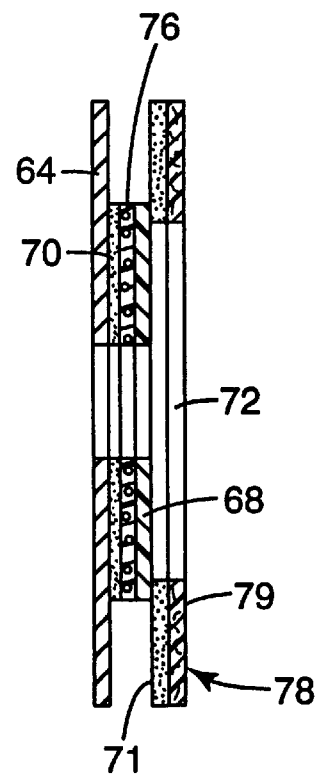
FIG. 14 is a cross-section view of the landing zone of FIG. 13, taken along line 14—14, illustrating the collar tape, the non-tacky surface layer, an optional gap filling layer, a pressure sensitive adhesive layer, and the liner used to protect and cover the pressure sensitive adhesives prior to use.

FIG. 14 is a cross-section view of the landing zone of FIG. 13, taken along line 14—14, illustrating the collar tape 78, the non-tacky surface layer 68, an optional gap filling layer 76, a pressure sensitive adhesive layer 70 used to help attach the landing zone to a patient, and the liner 64 used to protect and cover the pressure sensitive adhesives 71 and 70 prior to use. Collar 78 may comprise a backing 79 (e.g., a non-woven, elastic material) and a layer of pressure sensitive adhesive 71.

The contact responsive fastener system of the invention may be provided as a premated structure or, alternatively, in the form of separate components. In its various embodiments, it is useful for permitting multiple fastening and releasing of an article onto a structure, or for multiple fastening and releasing of a first article to a second article. The fastener and landing zone components each comprise a non-tacky surface layer. At least one of these surface layers comprises a contact responsive fastening layer.

Other uses include fastenings on disposable consumer goods requiring multiple closures, and clean room or medical and surgical garment fastenings. For example, they may be used with surgical gowns, drapes, and surgical gloves. A non-tacky fastener of the invention may be used to form a fluid resistant seal with a surgical glove. Drape uses include tube and cord organizers, repositionable plastic pouches, repositionable incisor areas, and attachments of repositionable drape parts. The advantages of the invention include low cost, non-tacky properties, thin profiles, compatibility with latex gloves, and adjustable peel strength. The fasteners can be made adjustable to allow for good fit and essentially complete seals at the junction of gloves and gowns to prevent contamination with bodily fluids. Non-tacky fasteners will not entangle the nonwoven hair coverings worn by surgeons and nurses.

EXAMPLES

The following examples are offered to aid in the understanding of the present invention and are not to be construed as limiting the scope thereof. Unless otherwise indicated, all parts and percentages are by weight. The following tests were used to measure the various test results reported in the examples.

T-Peel Strength

This test was used to determine the peel force required to cause two fastening components to release from each other when the substrate of a composite fastening component was a flexible film having a length of at least 20 cm and when pulling the edges of the fastener in opposite directions away from and perpendicular to the interface of the fastener bond. After two of the composite fastening components were placed in contact, the two components were engaged by means of a 2-kg hard-rubber roller, one pass in each direction. The engaged components were allowed to stand at ordinary room temperature (i.e., 22° C.) for the specified time period (hereinafter dwell time), one end of each component was secured to a jaw of an Instron tensile tester, and the jaws were moved apart at a rate of 30 cm/min.

180° Peel Strength

This test was run according to ASTM D-1000 except that the fastener component was applied to various surfaces using a 2-kg hard rubber roller, one pass in each direction. Samples were allowed to dwell for the specified time and temperature before being separated at a rate of 30 cm/min.

90° Peel Strength

This was run according to PSTC-5 using various rigid target surfaces to which the fastener component was applied using a 2-kg hard-rubber roller, one pass in each direction. Samples were allowed to dwell for the specified time and temperature before being separated at a rate of 30 cm/min.

Dynamic Shear Strength

Unless otherwise noted, this test was used to determine the amount of shear force required to either cause two fastening layers to release from each other or a fastening layer and a target surface to release from each other. A pair of 2.5 cm×10 cm strips was secured together with a 6.25 square centimeter overlap. The strips were engaged by means of a 2-kg hard-rubber roller, one pass in each direction. After the engaged strips were allowed to stand at ordinary room temperature for at least 30 seconds, one end of each strip was secured to a jaw of an Instron tensile tester, and the jaws were separated at a rate of 30 cm/min.

Static Shear Strength

This test was run essentially according to ASTM D-3654 and was used to determine the holding power of an assembled fastening layer to a target surface that was adhered to a rigid plate. A 2.5 cm×10 cm strip of fastener was secured to the mounted target surface using a 6.25 square centimeter overlap. The fastener and target surface were engaged by means of a 2-kg hard-rubber roller, one pass in each direction. The engaged strips were allowed to stand at ordinary room temperature for approximately 30 seconds. One end of each strip was secured to a 250 gram weight. The weight was allowed to hang supported by the fastener, and the amount of time until the sample fell was measured.

| | |
|---|---|
| ABS | Acrylonitrile-butadiene-styrene polymer |
| BACN | Butadiene-acrylonitrile polymer |
| BACNI | Butadiene-acrylonitrile-isoprene polymer |
| BOPP | Biaxially oriented polypropylene film |
| UA | Urethane acrylate polymer |
| SBS | Styrene-butadiene-styrene block copolymer |
| SIS | Styrene-isoprene-styrene block copolymer |
| CA | Cellulose Acetate |
| EVA | Ethylene vinylacetate polymer |
| HDPE | High density polyethylene |
| LDPE | Low density polyethylene |
| MEK | Methyl ethylketone |
| PA | Polyamide |
| PC | Polycarbonate |
| PE | Polyethylene |
| PET | Poly(ethylene terephthalate) |
| PMMA | Poly(methyl methacrylate) |
| PP | Polypropylene |
| PS | Polystyrene |
| PVC | Poly(vinyl chloride) |
| SS | Stainless steel |

The following abbreviations represent the commercially available materials used in the examples:

| | |
|---|---|
| BACN-1 | Nipol ™ DN-207, 33% acrylonitrile, Mooney viscosity of 43. |
| BACN-2 | Nipol ™ DN-004, 45% acrylonitrile, Mooney viscosity of 43. |
| BACN-3 | Nipol ™ DN-214, 33% acrylonitrile, Mooney viscosity of 80. |
| BACN-4 | Nipol ™ DN-401L, 19% acrylonitrile, Mooney viscosity of 65. |
| BACN-5 | Goodyear N-206, 45% acrylonitrile, Mooney viscosity of 60. |
| BACN-6 | HYCAR ™ 1022, 33% acrylonitrile, Mooney viscosity of 50. |
| BACNI-1 | Nipol ™ DN-1201L, believed to be approximately 52% butadiene, 33% acrylonitrile, and 15% isoprene, Mooney viscosity of 46 (chunk form). |
| BACNI-2 | Nipol ™ DN-1201L (with talc), believed to be approximately 52% butadiene, 33% acrylonitrile, and 15% isoprene, Mooney viscosity of 46 (crumb form with 3–7% magnesium silicate). |
| SBS | Kraton ™ 1101. |
| SIS | Kraton ™ 1107. |

The Nipol™ materials are available from Zeon Chemicals, Inc. and contain <1% antioxidant. The Goodyear materials are available from Goodyear Chemical Co. and contain <1% antioxidant. The HYCAR™ materials are available from B.F. Goodrich Chemicals and contain <1% antioxidant. The Kraton™ materials are available from Shell Chemical Company.

Example 1

Samples of BACN and BACNI-1 which contained an additional 1.5% by weight Ethanox™ 330 antioxidant (Ethyl Corporation) were dissolved in MEK solvent and then coated out onto a 0.05 mm primed polyester film backing to give a dry thickness of 0.83 mm. The samples varied in the proportion of acrylonitrile to butadiene and in Mooney viscosity. The Mooney viscosity reflects composition and molecular weight, i.e. extent of polymerization. Some of these samples contained 0.15% 2-(4-methoxyphenyl)-4, 6-bis (trichloromethyl)-1,3,5-triazine crosslinking agent. Some of the samples with the crosslinking agent were exposed to a high intensity medium pressure mercury arc light (Sylvania H33C0-400 boosted with a variable power source) at 600+watts. The dose was 150–200 millijoules/sq. cm.

T-peel and dynamic shear tests were performed on fastening layer to fastening layer samples. The first set of samples contained 33–34% acrylonitrile in the copolymer used as the fastening layer. It can be seen in Table 1 that all of the uncrosslinked samples blocked (irreversibly bonded) within one hour of contact.

TABLE 1

|  | Cross-linked | T-peel Strength (kN/m) #1 | #2 | #3 | #4 | #5 | #6 | #7 | Dynamic Shear Strength** (kN/m$^2$) |
| --- | --- | --- | --- | --- | --- | --- | --- | --- | --- |
| BACN-1 | No | 0.68 | 0.82 | 0.89 | Blocked* | 1.09 | 0.61 | 1.31 | 338 |
|  | Yes | 0.28 | 0.26 | 0.21 | 0.18 |  |  |  | 365 |
| BACN-6 | No | 0.30 | 0.53 | 0.77 | Blocked* |  |  |  | 359 |
|  | Yes | 0.39 | 0.37 | 0.28 | 0.26 | 1.28 | 0.56 | 1.58 | 234 |
| BACNI | No | 0.65 | 0.74 | 0.7 | Blocked* |  |  |  | 345 |
|  | Yes | 0.32 | 0.26 | 0.3 | 0.44 | 0.96 | 0.44 | 1.17 | 248 |

**Dynamic shear is measured after 1 minute of polymer face to polymer face contact (dwell time).
*Blocked in less than one hour.
1. T-peel force after 1 minute of dwell time.
2. Rebonded after #1 and measured after 1 more minute of dwell time.
3. Rebonded after #2 and measured after 1 more minute of dwell time.
4. Rebonded after #3 and measured after 4 more minutes of dwell time.
5. Rebonded after #4 and measured after 16 hours of dwell time.
6. T-peel force measured after 4 minutes of dwell time.
7. T-peel force measured after 16 hours of dwell time.

In a second set of samples, the acrylonitrile proportion of the polymer was varied from 19% to 45% and the Mooney viscosities were varied from 43 to 65. Initial peel forces did not vary significantly at short times between the crosslinked and the non-crosslinked samples.

For comparison, samples were made with SBS and SIS block copolymers. See the samples using SBS and SIS in Table 2.

TABLE 2

|  | Cross-linked | T-peel Strength (kN/m) 1 min | 2 min | 3 min | 22 hr | Dynamic Shear Strength* (kN/m$^2$) |
| --- | --- | --- | --- | --- | --- | --- |
| BACN-2 | No | 0.46 | 0.57 | 0.61 | Blocked | 286 |
|  | Yes | 0.56 | 0.67 | 0.64 | 1.75 | 379 |
| BACN-4 | No | 0.31 | 0.50 | 0.50 | 1.44 | 214 |
|  | Yes | 0.31 | 0.39 | 0.41 | 0.67 | 224 |
| BACN-5 | No | 0.18 | 0.25 | 0.29 | Blocked | 265 |
|  | Yes | 0.30 | 0.36 | 0.37 | 1.23 | 259 |
| SBS | No | 0.04 | 0.12 | 0.16 | 1.31 | 234 |
|  | Yes | 0.00 | 0.02 | 0.02 | 1.93 | 252 |
| SIS | No | 0.05 | 0.07 | 0.07 | 0.65 | 225 |
|  | Yes | 0.04 | 0.05 | 0.06 | 0.65 | 241 |

*Shear is measured after 1 minute of dwell time.

Crosslinking did not appear to decrease T-peel strength in the SBS and SIS samples after 22 hours of surface contact. Blocking was not observed in the SBS and SIS samples after 22 hours.

Example 2

In these samples, an electron beam was used to crosslink the non-tacky fastening layer. The example used uncrosslinked BACNI-2 and an additional 1.5% Ethanox™ 330 antioxidant in each sample. Experiments were performed to examine the effects of the voltage of the electron beam and the total dose of electrons.

Samples 2A–2F were hot melt extruded from a Haake extruder with a 5-inch (12.7 cm) wide film die. The temperature profile in the extruder was: die 175–180° C., zone 1 135–145° C., zone 2 135–145° C. zone 3 160–170° C. All hot melt coated samples were coated using these same extrusion conditions. The contact responsive fastening layers were coated onto a 0.127 mm thick spun bonded HDPE manufactured by DuPont under the trade name Tyvek™ 1073D films at a thickness of 5 mils (0.127 mm). Prior to coating, the Tyvek™ films were corona treated to improve the bonding of the rubber to the substrate. The T-peel strength results for six samples are given in Table 3:

TABLE 3

T-Peel Strength (kN/m)

| Dwell Time (min) | 2A | 2B | 2C | 2D | 2E | 2F |
|---|---|---|---|---|---|---|
| 0.5 | 0.10 | 0.15 | 0.04 | 0.04 | 0.01 | 0.00 |
| 1 | 0.17 | 0.18 | 0.05 | 0.06 | 0.02 | 0.00 |
| 2 | 0.23 | 0.26 | 0.07 | 0.07 | 0.04 | 0.00 |
| 5 | 0.52 | 0.36 | 0.11 | 0.08 | 0.06 | 0.00 |
| 12 Days | Blocked | Blocked | Blocked | Blocked | 0.53 | 0.04 |
| 0.5* | 0.13 | 0.19 | 0.07 | 0.03 | 0.04 | 0.00 |
| 1* | 0.13 | 0.25 | 0.10 | 0.06 | 0.05 | 0.00 |
| 2* | 0.16 | 0.27 | 0.13 | 0.08 | 0.05 | 0.00 |
| 5* | 0.23 | 0.25 | 0.14 | 0.08 | 0.07 | 0.00 |
| 0.5** | 0.11 | 0.13 | 0.06 | 0.04 | NT | NT |
| 1** | 0.11 | 0.15 | 0.08 | 0.05 | NT | NT |
| 2** | 0.17 | 0.19 | 0.09 | 0.07 | NT | NT |

*First Repeat. Surfaces of the fastener component stored unmated. Test repeated 12 days later.
**Second Repeat. Test repeated immediately following first repeat.
2A Exposed to 1 Mrad at 150 keV.
2B Exposed to 1 Mrad at 200 keV.
2C Exposed to 3 Mrad at 175 keV.
2D Exposed to 5 Mrad at 150 keV.
2E Exposed to 5 Mrad at 200 keV.
2F Exposed to 10 Mrad at 150 keV.

Exposure to 10 Mrad ($10^6$ rad) with an electron beam energy of 150 keV was sufficient to essentially remove all peel strength. Samples given lower exposures (i.e., less than 10 Mrad exposures) blocked after 12 days of surface contact except one sample given a dose of 5 Mrad with a beam energy of 200 keV.

Further experiments were performed to measure the effect of dose on the T-peel strength at shorter times. These samples were hot melt coated at a thickness of about 0.127 mm onto a backing comprised of 60% polyester and 40% cellulose with an acrylic binder (International Paper Co. Grade no. 1309215). The polymer in the samples contained 1.25% Agerite Staylite S antioxidant (R. T. Vanderbilt Co., product code 02909). The results for doses from 0.0 to 1.4 Mrads and an electron energy of 175 keV are shown in Table 4.

TABLE 4

T-Peel Strength (kN/m)

| Dose (Mrad at 175 keV) | 2E | 2F | 2G | 2H |
|---|---|---|---|---|
| 0 | 0.5690 | 0.7002 | 0.7002 | 0.7002 |
| 0.2 | 0.3764 | 0.4377 | 0.4814 | 0.5690 |
| 0.4 | 0.5515 | 0.6128 | 0.6303 | 0.7002 |
| 0.6 | 0.4814 | 0.5515 | 0.5952 | 0.6653 |
| 0.8 | 0.2801 | 0.3939 | 0.3939 | 0.5515 |
| 1.0 | 0.3939 | 0.4814 | 0.5252 | 0.6565 |
| 1.2 | 0.3064 | 0.3501 | 0.4027 | 0.5690 |
| 1.4 | 0.1751 | 0.2188 | 0.2451 | 0.2451 |

2E had 0.5 minute dwell time
2F had 1 minute dwell time
2G had 2 minutes dwell time
2H had 5 minutes dwell time

Example 3

In another test to ascertain the effect of crosslinking, chunks of about 6 cm×6 cm×12 cm of partly crosslinked BACN-4 were mixed with BACNI-2 in a ratio of 15% by weight to 85% by weight, respectively. About 1.25% Agerite Staylite S antioxidant was also added. Considerable mixing effort of the melted polymers was required to obtain uniform mixing of the two polymers. The mixture was hot melt coated as described in Example 2 at 5 mils (0.127 mm) thickness onto a backing of polyvinyl chloride (0.03 mm thick). The polymer face to polymer face T-peel strength (5 min. dwell time) was 0.48 kN/m for the mixture compared to 0.66 kN/m without any crosslinked polymer. On a backing of 60% polyester and 40% cellulose with a dwell time of five minutes, the peel force was 0.46 kN/m for the mixture compared with 0.70 kN/m without any crosslinked polymer.

Example 4

A comparison of four anti-blocking agents and samples with no anti-blocking agent was performed. Each sample used BACNI and a mixture of dry ingredients that included 1.5% by weight Cyanox™ LTDP (American Cyanamid), 1.5% by weight Irganox™ 1076 (Ciba Geigy), 0.25% by weight Tinuvin™ 328 (Ciba Geigy), and 0.25% by weight Tinuvin™ 770 (Ciba Geigy). A 0.127 mm thick fastening layer was hot melt coated as described in Example 2 onto about 0.05 mm primed PET film. Samples 4A, 4B, 4C and 4D used BACN-1. Sample 4E used BACN-2. Samples of BACNI-1 were used with the other anti-blocking agents. Unfastened samples were exposed to air, fluorescent room light and dust for up to 7 days. The test results are shown in Table 5 are based on a 5-minute room temperature dwell. Sample 4A employed no anti-blocking agent. Samples 4B, 4C, 4D and 4E employed 2.5% by weight Cab-O-Sil™, 1% by weight $CaSiO_4$, 1% by weight $CaCO_3$ and 5% extra talc, respectively.

TABLE 5

Initial T-Peel Strength/% Initial T-Peel Strength After Exposure

| Exposure Time (Days) | 4A | 4B | 4C | 4D | 4E |
|---|---|---|---|---|---|
| 0 | 0.5252/ 100% | 0.3064/ 100% | 0.4377/ 100% | 0.6128/ 100% | 0.7441/ 100% |
| 1 | 0.1751/ 33% | 0.1313/ 42.9% | 0.3501/ 80% | 0.1663/ 27.1% | 0.6128/ 82.4% |
| 4 | 0.0910/ 17.3% | 0.1401/ 45.7% | 0.0613/ 14% | 0.1050/ 17.1% | 0.1401/ 18.8% |
| 7 | 0.0088/ 1.67% | 0.0700/ 22.9% | 0.0175/ 4.0% | 0.0263/ 4.3% | 0.0193/ 2.6% |

The initial T-peel strength of these samples are shown as the top value (kN/m)in each box and the % of initial T-Peel strength is shown as the bottom number. These results demonstrate loss of initial T-peel strength with exposure. Sample 4B (2.5% Cab-O-Sil™ $SiO_2$, Cabot Corp.) anti-blocking agent gave the best results. The other anti-blocking agents were $CaSiO_4$ (Hubersorb 600, J. M. and $CaCO_3$ (Atomite, ECC International).

Some degree of crosslinking can be obtained by hot melt extruding BACN or BACNI. The exact amount of crosslinking was not determined. This example demonstrates that low peel strengths can be obtained from hot melt extruded samples with or without addition of antiblocking agents. Anti-blocking agents can be added to control the fastening properties. Combining partial crosslinking from hot melt extrusion with the addition of fillers provides an easy way to obtain a greater range of fastening properties than had been possible previously.

Example 5

The effect of the thickness of the fastening layer was measured. BACNI-2, which had 2% Agerite Staylite S was hot melt coated as described in Example 2 onto either 0.05 mm primed PET film or Guilford tricot knit cloth, style #15771. The samples were tested after a 2 minute dwell time at room temperature. The results are shown in Table 6.

TABLE 6

| Backing | Fastening Layer Thickness (mm) | T-Peel Strength (k/N/m) |
| --- | --- | --- |
| Primed PET | 0.05 | 0.2854 |
| Primed PET | 0.075 | 0.3764 |
| Primed PET | 0.10 | 0.4464 |
| Primed PET | 0.13 | 0.5830 |
| Tricot cloth | 0.10 | 0.0735 |
| Tricot cloth | 0.13 | 0.1488 |
| Tricot cloth | 0.20 | 0.3501 |

The results show linear increases in the value of peel strength with coating thickness over the thicknesses examined.

Example 6

Further experiments were performed to show the effect of surface texture on peel strength. BACNI-2 containing 1.5% by weight Cyanox™ LTDP, 1.5% by weight Irganox™ 1076, 0.25% by weight Tinuvin™ 328 and 0.25% by weight Tinuvin™ 770 was hot melt coated as described in Example 2 to a thickness of 5 mils (0.127 mm) onto 0.05 mm thick primed PET film. The still hot polymer-coated film was passed between two rolls of a nip. A smooth surface was produced using a 0.051 mm BOPP film between the roller and polymer. A "rubber roller matte" surface was introduced just by passing the hot polymer directly through the rubber rollers. An even rougher surface, i.e., textured matte, was produced by placing a textured film between the roller and the hot rubber. Table 7 compares T-peel strength at various dwell times up to five minutes. The smooth surface gives the highest strength, and the textured matte surface gives the lowest strength. These results indicate that the peel strength varies with the amount of surface contact.

TABLE 7

| Surface | Dwell Time (Min) | T-Peel Strength (kN/m) |
| --- | --- | --- |
| Smooth | 0.5 | 0.5690 |
| Smooth | 1.0 | 0.8754 |
| Smooth | 2.0 | 0.9156 |
| Smooth | 5.0 | 0.9979 |
| Rubber matte | 0.5 | 0.4814 |
| Rubber matte | 1.0 | 0.6128 |
| Rubber matte | 2.0 | 0.7528 |
| Rubber matte | 5.0 | 0.7528 |
| Textured matte | 0.5 | 0.1751 |
| Textured matte | 1.0 | 0.2171 |
| Textured matte | 2.0 | 0.2171 |
| Textured matte | 5.0 | 0.2171 |

Example 7

Guilford Knit cloth, style #15771, was hot melt coated as described in Example 2 with a 0.203 mm thick layer of BACNI-2 containing 2% Agerite Staylite™ S antioxidant. Half of the samples were covered with a 0.102 mm thick PE liner. The other half of the samples were left uncovered.

The covered (i.e., linered) and uncovered (i.e., unlinered) samples were tested for T-Peel strength under various conditions. In a first set of experiments, some of the unlinered samples were exposed to fluorescent room light, air and dust. Others of the unlinered samples were protected from fluorescent light and dust by being placed in a Bell Jar. Initially, all of the samples had a T-Peel strength of 0.79 kN/m. Those unlinered samples that were not protected from the exposure to fluorescent light and dust lost virtually all strength by 18 days. Those unlinered samples that were in the Bell Jar retained a T-Peel strength of about 0.35 kN/m after 10 months.

In a second set of experiments, linered and unlinered samples were exposed to UV light (2 mW/cm$^2$) for varying times and then tested for T-Peel strength after a 5-minute dwell time. The results of these tests are shown in Table 8.

TABLE 8

| Sample | Time Under UV Light (Hrs.) | Total Exposure (mJ) | T-Peel Strength (kN/m) |
| --- | --- | --- | --- |
| Linered | 0 | 0 | 0.79 |
| Linered | 2 | 1,440 | 0.44 |
| Linered | 5.5 | 3,960 | 0.175 |
| Linered | 7 | 50,400 | 0.0875 |
| Linered | 9 | 64,800 | 0.0595 |
| Linered | 11 | 79,200 | 0.051 |
| Unlinered | 0 | 0 | 0.79 |
| Unlinered | 1.5 | 10,800 | 0.432 |
| Unlinered | 3 | 21,600 | 0.201 |
| Unlinered | 7 | 50,400 | 0.0928 |

The implication is that a major part of the loss of peel strength with time is due to ultraviolet light induced oxidation when a sufficient amount of an effective antioxidant is not present. A variety of antioxidants and UV stabilizers can be used to minimize or eliminate UV light induced oxidation. Addition of stabilizers during the manufacture of the polymer would be the best approach for blending the antioxidant and UV stabilizers for hot melt extrusion or any type of coating process.

Example 8

This example illustrates that the peel strength of a fastener system can be controlled by selecting the properties of the target surface to which the contact responsive fastening layer is attached. The example shows that varying the solubility parameter of the target surface by selecting the target surface from a range of materials permits one to control the peel strength of the fastening system.

BACN-6 was dissolved in MEK and then solvent-coated onto a 0.025 mm thick corona treated polyester backing to give a nominal dry thickness of 0.017 mm. The resulting fastening layer was tested for 180° peel strength from a variety of smooth target surfaces. A 10-minute dwell time at room temperature (21° C.) was used. Table 9 demonstrates the variation of 180° peel force as a function of the solubility parameter of the smooth target surface. Where available, single point values were used instead of ranges. The solubility parameter of BACN-6 was not itself measured. However, the solubility parameter for a 70% butadiene, 30% acrylonitrile is in the range of 9.38–9.48 (cal/ml)$^{1/2}$. It was assumed that the solubility parameter for BACN-6 would be essentially the same.

TABLE 9

| Target Surface | Solubility Parameter (cal/ml)$^{1/2}$ | 180° Peel Strength (kN/m) |
|---|---|---|
| PE | 7.9 | 0 |
| PP | 8.7* | 0.197 |
| PS | 9.1 | 0.81 |
| PMMA | 9.2 | 1.1489 |
| PVC | 9.5 | 1.2583 |
| PC | 9.5 | 1.2583 |
| PET | 10.7 | 0.569 |
| Epoxy | 10.9 | 0.3392 |
| CA | 13.4 | 0.0547 |
| Nylon | 13.6 | 0.0438 |

*This represents the mid-point of the range of solubility parameters found in the open literature.

Table 9 demonstrates that the 180° peel strength of a fastener prepared from BACN can be varied by appropriate choice of solubility parameter of the target surface material used to attach to the non-tacky fastening layer.

Example 9

BACNI-2 was hot melt coated onto a 1.7 mil (0.043 mm) thick unplasticized poly vinyl chloride (UPVC) film at a 7.3 mil (0.185 mm) coating thickness as described in Example 2. The polymer contained from 3–7% talc. The resultant fasteners were then tested for 90° peel strength after a 3-day dwell time against various target surfaces to study the effect of solubility parameter on peel strength. The DuPont Base Coat/Clear Coat 871/RK7103 and the White High Solids Enamel BASF E172 were tested after a somewhat different dwell time than the other samples. The 22° C. dwell time was 24 hours. The elevated temperature dwell time was 46 hours at 70° C. Table 10 shows the variation of the 90° peel strength depending on the target surface mated with the non-tacky fastening layer at two different temperatures.

TABLE 10

90° Peel Strength (kN/m)

| Target Surfaces | Temperature 22° C. | Temperature 49° C. | Dwell Time (Hr.) |
|---|---|---|---|
| PC | 3.02 | 2.98 | 72 |
| ABS | 3.50 | 3.94 | 72 |
| PMMA | 2.98 | 3.37 | 72 |
| PA | 0.70 | 3.50 | 72 |
| Glass | 0.21 | 0.24 | 72 |
| EVA | 0.40 | 0.42 | 72 |
| PET | 0.32 | 0.39 | 72 |
| Corona Treated PET | 0.36 | 0.44 | 72 |
| LDPE | 0.03 | 0.04 | 72 |
| HDPE | 0.03 | 0.04 | 72 |
| SURLYN ™ | 0.09 | 0.13 | 72 |
| PS | 0.03 | 0.04 | 72 |
| DuPont Base Coat/ Clear Coat 871/RK7103 | 0.23 24 hr. | 0.21 46 hr. 70° C. | 24 hr RT 46 hr. 70° C. |
| White High Solids Enamel BASF E172 | 0.20 24 hr. | 0.20 46 hr. 70° C. | 24 hr RT 46 hr. 70° C. |

Example 10

Samples of uncrosslinked BACNI-1 containing 2% by weight Irganox™ 1010 antioxidants were solvent coated as described in Example 1 onto one side of a 0.0021 mm thick primed PET which had a 0.05 mm thick tacky pressure sensitive adhesive. The adhesive was covered with a paper liner on the opposite side. The resultant fasteners were then tested for 90° peel strength at room temperature to various target surfaces after a one-day dwell time at 22° C. and 70° C. to study the effect of solubility parameter on peel performance. The results are given in Table 11.

TABLE 11

90° Peel Strength (kN/m)

| Target Surface | 22° C. | 70° C. |
|---|---|---|
| SS | 0.236 | 0.336 |
| PC | 1.138 | 1.313 |
| PMMA | 1.138 | 1.251 |
| PP | 0.145 | 0.123 |
| HDPE | 0.053 | 0.053 |
| LDPE | 0.044 | 0.039 |
| PS | 0.648 | 0.648 |
| ABS | 1.750 | 1.260 |
| Rigid Filled PVC | 0.508 | 1.496 |
| Glass | 0.161 | 0.149 |
| DuPont Base Coat/Clear Coat 871/RK7103 | 0.341 | 0.257 |
| White High Solids Enamel BASF E172 | 0.350 | 0.257 |
| BOPP | 0.123 | 0.136 |

Example 11

A fastening system according to the invention was prepared as follows. A composition containing 70% by weight acrylate capped polycaprolactone urethane oligomer, 30% by weight isooctyl acrylate, and 0.25% 1-hydroxycyclohexyl acetophenone was coated onto one side of a 0.036 mm UPVC film which had a 0.05 mm tacky pressure sensitive adhesive layer with a paper liner on the opposite side. The fastening layer was cured with 240–280 mJ of high intensity ultraviolet light through a filter which removed wavelengths below 300 nm. The samples were cured through a 0.05 mm BOPP cover film to prevent oxygen inhibition.

The resultant fastening system was tested for 90° peel strength at room temperature against various surfaces after a 24 hr dwell at 22° C. and 46 hr dwell at 70° C. The results are given in Table 12.

TABLE 12

90° Peel Strength (kN/m)

| Target Surfaces | 24 hr 22° C. | 46 hr 70° C. |
|---|---|---|
| SS | 0.324 | 0.560 |
| PC | 0.499 | 0.446 |
| PMMA | 0.481 | 0.450 |
| PP | 0.023 | 0.012 |
| HDPE | 0.026 | 0.013 |
| LDPE | 0.016 | 0.014 |
| PS | 0.219 | 0.096 |
| ABS | 0.494 | 0.502 |
| Rigid Filled PVC | 0.516 | 0.630 |
| Glass | 0.350 | 0.411 |
| DuPont Base Coat/Clear Coat 871/RK7103 | 0.205 | 0.288 |
| White High Solids Enamel BASF E172 | 0.210 | 0.228 |

Example 12

Butyl rubber (Chlorobutyl 1255, Polysar Rubber Corp.) was solvent coated from a 25% solution in hexane to a thickness of about 0.063 mm onto a 0.0254 mm thick corona treated PET. The resultant fastener was then tested for 90° peel strengths at room temperature against a variety of surfaces after a dwell time of 3 hours at 22° C. The results are given in Table 13.

TABLE 13

| Target Surface | 90° Peel Strength (kN/m) |
|---|---|
| White painted metal | 0.4025* |
| Blue painted metal | 0.21875 |
| HDPE | 0.0875 |
| LDPE | 0.0875 |
| PVC | 0.105 |
| PC | 0.30625 |
| PMMA | 0.48125* |
| SS | 0.245 |
| Glass | 0.21 |

*The peel strength was greater to the substrate than to the backing.

Table 13 shows the same principle of varying the adhesive force by altering the material on the target surface. The fastening layer exhibited slight finger tack. Also, it should be noted that fillers may be added to reduce tackiness. This is especially true with butyl rubbers.

Example 13

Sample articles were made with hot melt extruded BACNI-2 and ultraviolet curable UA (Example 11). These samples had satisfactory peel and shear. The BACNI-2 can be mated to PET or BOPP if not sufficiently crosslinked to prevent blocking to itself. The ultraviolet cured UA maintained adhesion after ETO (ethylene oxide gas) sterilization. Some peel performance was lost after 2–3 Mrads of Gamma sterilization. The BACNI-2 had acceptable fastener performance after 10 Mrads of Gamma sterilization when exposed while in contact with a liner or a BOPP target surface.

Example 14

A Quick Tack measuring system was utilized to measure the peel force of a set of the non-tacky fastening layer and certain pressure sensitive adhesives. The peel force is measured at a ninety degree angle from the surface where any peel force results just from contact with essentially no external pressure added other than the weight of the tape. An IMASS tensile tester with a 0.455 kg load cell was employed. Several fastening layer materials disclosed above were tested: (1) BACNI-1 polymer, (Example 10 at 0.021 mm thickness), (2) UA (Example 11) at 0.02 cm thickness, and (3) a tackified block copolymer comprising 75% by weight Kraton G1657 (styrene-ethylene-butadiene-styrene (SEBS)) and 25% by weight Regalrez™ 1085 at 0.013 cm thickness (M). In addition, the low tack repositionable pressure sensitive adhesive composition (Scotchbrand Differential Tack Double Coated Tape 9415 with Post-it™ adhesive on one side) from 3M was also tested. The results of these tests are set out in Table 14. These samples were also subjectively measured for their tack to skin. As shown in Table 14, samples BACNI, UA, and M were non-tacky to skin. The Post-It™ adhesive, in contrast, felt tacky.

TABLE 14

|  | BACNI | UA | M | Post It ® Adhesive |
|---|---|---|---|---|
| Bondpaper[a] | 0.0004 | 0.0000 | 0.0008 | 0.244 |
| Newspaper[b] | 0.0000 | 0.0000 | 0.0000 | 0.0152 |

TABLE 14-continued

|  | BACNI | UA | M | Post It ® Adhesive |
|---|---|---|---|---|
| Legal Pad[c] | 0.0000 | 0.0000 | 0.0000 | 0.0044 |
| Skin | Non-tacky | Non-tacky | Non-tacky | Tacky |

[a]Bondpaper, 3M Copy White Bond Paper, Stock No. 78-6969-6135.
[b]Newspaper, Minneapolis Star Tribune 2/22/93 non-inked portion.
[c]Legal Pad, St. Paul Book and Stationary Stock No. 91242-969.

This demonstrates the essentially no-tack characteristic of the M, UA, and BACN fastener layer materials as compared with the tack (although generally known as an example of a low tack material) of the Post It® adhesive.

Example 15

Contact responsive fastener systems perform best when both the fastening layer and target surface are smooth surfaces. A Surface Roughness Test was used to measure the smoothness. In Table 15 the averages of the absolute departures from the centerline of the roughness profile of a surface for a variety of non-tacky fastener and target surfaces.

TABLE 15

|  | Microns |
|---|---|
| 0.014 mm mil PET film | 0.042 |
| 0.051 mm BOPP film | 0.033 |
| White bond copier paper | 1.5 |
| Glass | 0.01 |
| 0.051 mm UV cured UA | 0.297 |
| 0.021 mm mil solvent coated BACNI-1 | 0.376 |
| 0.127 mm hot melt coated BACNI-2 | 0.326 |
| Texture hot melt coated BACNI-2 | 1.1 |
| 0.013 mm solvent coated SEBS (75/25 ratio) | 0.12 |

Example 16

Tests were performed to examine the effect of a large number of unfastening and refastening operations on the 90° peel force. Tests were performed with non-tacky fastener coated onto 0.036 mm UPVC that was attached with 0.051 mm tacky pressure sensitive adhesive to a 0.014 mm PET support. The 90° peel forces were measured with a 2.54 cm wide strip of non-tacky fastener using a one minute dwell time. Table 16 shows the results for 0.021 mm thick solvent coated BACNI-1 peeled from a glass target panel and 0.051 mm thick UA peeled from a PMMA target panel. After each one hundred peels, the adhesives were rolled against the desired target panel with a 2 kg. roller using one pass in each direction.

TABLE 16

| | 90° Peel Strength (kN/m) Fastener Layer/Target Surface | |
|---|---|---|
| Cycle No. | BACNI/Glass | UA/PMMA |
| 1 | 0.11 | 0.20 |
| 100 | 0.11 | 0.18 |
| 200 | 0.11 | 0.16 |
| 300 | 0.13 | 0.15 |
| 400 | 0.14 | 0.25* |
| 500 | 0.17 | 0.24 |
| 600 | 0.17 | 0.27 |
| 700 | 0.17 | 0.20 |
| 800 | 0.18 | 0.22 |

TABLE 16-continued

90° Peel Strength (kN/m)
Fastener Layer/Target Surface

| Cycle No. | BACNI/Glass | UA/PMMA |
|---|---|---|
| 900 | 0.16 | 0.22 |
| 1000 | 0.17 | 0.19 |
| 1100 | 0.16 | 0.19 |
| 1200 | 0.16 | 0.18 |
| 1300 | 0.15 | 0.18 |
| 1400 | 0.15 | 0.17 |
| 1500 | 0.15 | 0.17 |
| 1600 | 0.16 | 0.16 |
| 1700 | 0.16 | 0.17 |
| 1800 | 0.15 | 0.15 |
| 1900 | 0.14 | 0.14 |
| 2000 | 0.14 | 0.15 |

*Test stopped after 300 cycles and restarted about 24 hours later.

The data in this Table show the relatively low and constant peel strength over multiple releases and refastenings of the fastening system of the invention.

Example 17

Two samples of urethane (UR) non-tacky fasteners were prepared. The UR was coated out as a fastening layer on UPVC.

The urethanes were prepared by heating polyol(s) in a glass jar at 70° C. until melted, adding an isocyanate-containing component with stirring until well blended, and then adding 4 drops of a 1% solution by weight of dibutyltin dilaurate (DBTDL) in propylene glycol monomethyl ether acetate (PM Acetate from Union Carbide). The resultant urethanes were cast as a 0.10 mm (4 mils) thick layer on one side of 0.05 mm (2 mils) thick UPVC film that had a pressure sensitive adhesive on the other side. The resultant tape was then cured at 74° C. for 24 hours and allowed to dwell at room temperature for about 1 week before testing for 90° peel against various target surfaces.

The ingredients used to make the UR and the 90° peel test results are given in Table 17 below. The quantities of the ingredients are reported in parts by weight. The samples had no tack when tested against paper.

TABLE 17

| Ingredient | Sample A | Sample B |
|---|---|---|
| Tone ™ 200 | 100 | 36.7 |
| Tone ™ 310 | — | 31.2 |
| IPDI | 39.9 | — |
| MPCHI | — | 32.1 |
| 90° Peel Strength (kN/m) | | |
| 2 min. dwell @ RT | | |
| (a) to self | 0.028 | 0.016 |
| (b) to glass | 0.087 | 0.061 |
| 24 hr. dwell @ RT | | |
| (a) to self | 0.525 | 0.044 |
| (b) to glass | 0.096 | 0.105 |
| (c) to SS | 0.087 | 0.149 |
| 46 Hr. dwell @ 70° C. | | |
| (a) to self | 1.93 | 0.121 |
| (b) to glass | 0.788 | 0.376 |
| (c) to SS | 1.24 | 0.481 |

Tone™ 200 is a difunctional caprolactone polyol, MW 530, commercially available from Union Carbide Corporation, Danbury, Conn. Tone™ 310 is a trifunctional caprolactone polyol, MW 900, commercially available from Union Carbide Corporation, Danbury, Conn. IPDI is isosphorone diisocyanate, commercially available from Huils, Germany. MPCHI is methylene bis (4-cyclohexylisocyanate), commercially available as Desmodur™ W from Mobay Chemical Corporation (now known as Miles, Inc.), Pittsburgh, Pa.

Example 18

Six samples of acrylic (AC) non-tacky fasteners were prepared. The AC compositions were each coated out as a fastening layer on primed PET.

The acrylic compositions were prepared by solution polymerization as outlined in U.S. Pat. No. Re. 24,906 (Ulrich) using a 40% solids content solution of the monomers and ethyl acetate, 0.3% 2-2'-azobis(isobutyronitrile) initiator (Vazo® 64, commercially available from E. I. duPont de Nemours) and heating the mixture at 55° C. for 24 hours. The resultant acrylic compositions were each cast as a film which had a dry thickness of about 0.025 mm (1 mil) onto a 0.038 mm (1.5 mils) primed PET. The resultant tape was allowed to equilibrate at RT for about 24 hours before testing for T-peel strength against various target surfaces.

The sample compositions are given in Table 18. Fastening layers, target surfaces, and T-peel test results are reported in Table 19. The quantities of ingredients are reported in parts by weight. The samples had no tack when tested against paper.

TABLE 18

| | Parts by Weight Monomer | | | | | | |
|---|---|---|---|---|---|---|---|
| Monomer | AC1 | AC2 | AC3 | AC4 | AC5 | AC6 | AC7 |
| Ethyl acrylate | 70 | 60 | — | — | — | — | — |
| Butyl acrylate | 20 | 30 | 40 | 40 | 20 | 10 | — |
| Acrylic acid | 10 | 10 | — | — | — | — | — |
| Isobornyl acrylate | — | — | 50 | 50 | — | — | — |
| 2-Sulfoethylmethacrylate | — | — | 10 | — | — | — | — |
| 2-Acrylamido-2-methyl-propane sulfonic acid | — | — | — | 10 | — | — | — |
| Methyl acrylate | — | — | — | — | 70 | 80 | — |
| Dimethylaminoethylmethacrylate | — | — | — | — | 10 | 10 | 10 |
| Ethyl acrylate | — | — | — | — | — | — | 90 |

TABLE 19

| Fastening Layer/ | T-Peel Strength (kN/m) | |
|---|---|---|
| Target Surface | 2 minute RT dwell | 1 week RT dwell |
| AC1/AC1 | 0.289 | 0.641 |
| AC2/AC2 | 0.287 | 0.588 |
| AC3/AC3 | 0.737 | 0.852 |
| AC4/AC5 | 0.238 | 0.334 |
| AC4/AC6 | 0.238 | 0.3185 |
| AC4/AC7 | 0.229 | 0.313 |

Example 19

A sample of a polyethylene copolymer blend composition (P) was extruded out as a fastening layer.

The composition was prepared by dry mixing together equal parts by weight polyethylene copolymer (85% ethylene and 15% butene with 0.8% by weight of microtalc) (DFDB 1085, commercially available from Union Carbide, Danbury, Conn.) and polyethylene copolymer (96% ethylene and 4% octene) (LLDPE 6806, commercially available from Dow Chemical Co., Midland, Mich.) and feeding the mixture through an extruder and single layer die (both extruder and die at a temperature of about 220° C.) to yield a 0.076 mm thick layer. From the die the layer was carried on a chrome casting roll (roll temperature 10° C. to 23° C.) to a windup roll where the layer was wound around a paper core. The resultant roll was allowed to dwell at RT for about 4 months before testing for 90° peel strength against various target surfaces.

Target surfaces and 90° peel test results are reported in Table 20 below. The samples had no tack when tested against paper.

TABLE 20

| Target Surface | 90° Peel Strength (kN/m) | |
|---|---|---|
| | 2 minute RT dwell | 1 week RT dwell |
| Self | 0.083 | 0.072 |
| PC | 0.039 | 0.038 |
| PVC | 0.013 | 0.0185 |
| SS | 0.0375 | 0.021 |
| ABS | 0.011 | 0.027 |
| HDPE | 0.002 | 0.014 |
| LDPE | 0.014 | 0.024 |
| PP | 0.019 | 0.155 |
| PS | 0.000 | not tested |

Example 20

BACNI-1 was hot melt coated onto a silicone coated paper liner at a coating thickness of 2.5 mil (0.064 mm). The BACNI-1 layer was then laminated to one side of a 0.92 mil (0.023 mm) thick white PET film. The backside of the PET film was then coated with a 0.05 mm thick layer of a pressure sensitive adhesive. The resultant fastening component ("F-20") was then tested for peel strength, dynamic shear strength, and static shear strength against various target surfaces. The above fastening components were tested immediately after being placed in contact with the target surface and after 48 hours dwell time.

Several two-piece ostomy bags were made using commercially available ostomy pouches to which the above fastening component, F-20, was attached via a layer of tacky pressure sensitive adhesive. The fastening component was cut to form a 67 mm diameter circle in which a small "starter hole" was placed at the center. Several different landing zone materials were evaluated. Some of these landing zone materials have found use in other existing medical products and are believed to be safe and efficacious for use on skin. These different materials were selected so as to be able to evaluate a variety of different adhesion levels for use in ostomy application. If desired, one could alternatively adjust the adhesion level by varying the fastening layer of the fastening component.

Each prototype device consists of a pouch, a fastener and a landing zone material. A commercially available tacky tape material having a polyethylene/EVA copolymer backing and a tacky acrylate adhesive (available from 3M Co., St. Paul, Minn. as #9835) was chosen as a control. This tacky tape has been shown to provide acceptable adhesion for ostomy pouches.

Two prototype pouches were filled with 200 ml of water and vertically suspended on a target surface to assess the resistance of the connection to slippage due to shear forces and to determine the removability of the pouch from the landing zone multiple times over a several-day period. Both prototype pouches were constructed using the F-20 fastener. One prototype used the "9835 tape" for the landing zone. This prototype was also subjected to manual "sloshing" of the water in the pouch so that the fastener/landing zone interface was exposed to moisture. A second prototype utilized a landing zone that has a polyurethane backing. Both prototypes performed extremely well in the holding of the pouch for several days. The first prototype also performed well even when water was sloshed on the interface. The fastener of the second prototype showed a very high peel force necessary to remove it from the polyurethane landing zone after 24 hours. The fastener of the first prototype was easily removed from and reattached to the "#9835" landing zone multiple times during a two-week period.

Testing was also done in which various landing zone materials were coupled with the F-20 fastener. As a control, the various landing zone materials were also adhesively coupled with the sticky adhesive surface of the #9835 medical tape. Peel strength, dynamic shear strength and static shear strength were measured at initial bonding. Peel strength and dynamic shear strength were also tested after the compositions were exposed to 38° C. for 48 hours to simulate the body temperature when a collection device is worn. The test sample identification and the results of the testing are shown in the following tables.

TABLE 21

| Run # | Fastener | Landing Zone |
|---|---|---|
| 1 | F-20 | 9835[1] |
| 2 | F-20 | 1516[2] |
| 3 | F-20 | MSX-1389[3] |
| 4 | F-20 | MSX-3076[4] |
| 5 | F-20 | F-20 |
| C1 | 9835 | 9835 |
| C2 | 9835 | 1516 |
| C3 | 9835 | MSX-1389 |
| C4 | 9835 | MSX-3076 |
| C5 | 9835 | F-20 |

[1]9835 tape has a polyethylene/EVA copolymer backing, and a layer of a tacky acrylate pressure-sensitive adhesive (available from 3M, St. Paul, MN).
[2]1516 tape has a polyester film backing with release coating, and a tacky acrylate pressure-sensitive adhesive (available from 3M).
[3]MSX-1389 tape has a polyurethane backing, and a tacky acrylate pressure-sensitive adhesive (available from 3M).
[4]MSX-3076 tape has a polyurethane backing with release coating, and a tacky acrylate pressure-sensitive adhesive (available from 3M).

TABLE 22

| | Initial Testing Results at R.T. | | |
|---|---|---|---|
| Run # | 180° Peel (kN/m) | Dynamic Shear Strength (kN/m$^2$) | Static Shear Strength (Minutes) |
| 1 | 0.011 | 42.4 P | >1100* |
| 2 | 0.011 | 105.4 P | >1700 |
| 3 | 0.013 | 82.7 P | >1700 |
| 4 | 0.011 | 6.9 P | >1700 |
| 5 | 0.900 | blocked | >1700 |
| C1 | 0.08 | blocked | >1700 |
| C2 | 0.07 | 52.4 P | >1700 |
| C3 | 0.14 | blocked | >1700 |
| C4 | 0.05 | 31.7 P | >1700 |
| C5 | 0.09 | 56.5 P | >1700 |

TABLE 23

Testing Results After 48 Hours at 38° C.

| Run # | 180° Peel Strength (kN/m) | Dynamic Shear Strength (kN/m²) | |
|---|---|---|---|
| 1 | 0.044 | 42.0 | P |
| 2 | 0.022 | 128.8 | P |
| 3 | 0.292 | blocked | |
| 4 | 0.039 | blocked | |
| 5 | 1.740 | blocked | blocked |
| C1 | 0.30 | 53.1 | P |
| C2 | 0.16 | 62.0 | P |
| C3 | 1.33 | blocked | blocked |
| C4 | 0.22 | blocked | |
| C5 | 0.12 | blocked | |

Values with "P" indicate that pop-off occurred before clean failure of sample. "Blocked" describes when two components cannot be separated without destruction of one or more components.

One of triple replicates failed at 6 minutes, the other two held at least 1700 minutes.

TABLE 24

| | 90° Peel Strength (kN/m) | |
|---|---|---|
| Run # | 10 minutes dwell | 21 hours dwell |
| 1 | 0.82 | 1.57 |
| 3 | 0.62 | 11.8 |
| 4 | 0.30 | 0.42 |
| C1 | 8.7 | 12.7 |
| C3 | 5.5 | >19.6 |
| C4 | 3.3 | 19.6 |

Overall the performance of the F-20 fastener with the various landing zones was excellent. Very high shear strengths were measured for all the different landing zones. Each combination is expected to meet the performance requirements for ostomy applications.

Various modifications and alterations of this invention will be apparent to those skilled in the art without departing from the scope and spirit of this invention, and it should be understood that this invention is not limited to the illustrative embodiments set forth herein.

What is claimed is:

1. An ostomy appliance, comprising:
   a bag with an opening for receiving material from a stoma, and
   a fastening system comprising (i) a fastener attached to the bag circumscribing the opening and (ii) a landing zone, the fastening system having a non-tacky target surface layer, a contact responsive non-tacky fastening layer that adheres to the non-tacky target surface layer, and a means for attaching the fastening system to the peristomal area of a user.

2. The ostomy appliance of claim 1, wherein the means for attaching the fastening system to the peristomal area of a user comprises a layer of a tacky adhesive.

3. The ostomy appliance of claim 1, wherein the fastening layer is multiply releasable and refastenable against the target surface layer.

4. The ostomy appliance of claim 1, wherein the fastening layer has a 90° peel strength of less than about 3 kN/m and a dynamic shear strength of greater than 2 kN/m² when in contact with the target surface.

5. The ostomy appliance of claim 1, wherein the fastening layer is cleanable with retention of fastening characteristics.

6. The ostomy appliance of claim 1, wherein the fastening layer comprises a composition selected from the group consisting of homopolymers, random copolymers, block copolymers, and graft copolymers.

7. The ostomy appliance of claim 1, wherein the fastening layer comprises a polymer of from about 10 to about 50 weight percent of acrylonitrile and about 50 to about 90 weight percent of at least one of butadiene and isoprene, the polymer having a Mooney viscosity of from about 20 to about 95.

8. The ostomy appliance of claim 1, wherein the fastening layer comprises a crosslinked oligomeric resin having one or more like or different hard segments, and one or more like or different soft segments, and one or more like or different monovalent moieties containing a radiation-sensitive, addition-polymerizable, functional group.

9. The ostomy appliance of claim 1, wherein the fastening layer has essentially no adhesion to paper.

10. The ostomy appliance of claim 1, wherein the fastening layer comprises crosslinked butadiene-acrylonitrile polymer.

11. The ostomy appliance of claim 1, wherein the fastening layer comprises butadiene-acrylonitrile-isoprene polymer.

12. The ostomy appliance of claim 11, wherein the butadiene-acrylonitrile-isoprene polymer comprises up to about 30 weight percent isoprene.

13. The ostomy appliance of claim 1, wherein the target surface comprises another non-tacky fastening layer.

14. The ostomy appliance of claim 2, wherein the fastening layer is permanently attached to the bag and forms the fastener, and the target surface and adhesive layer are provided as the separable landing zone component.

15. The ostomy appliance of claim 14, wherein the fastener further comprises a mounting layer comprising a pressure sensitive adhesive.

16. The ostomy appliance of claim 15, wherein a backing layer is interposed between the fastening layer and the mounting layer.

17. The ostomy appliance of claim 1, wherein a covering layer is removably attached to the fastening layer.

18. The ostomy appliance of claim 1, wherein the fastener is attached to the bag by an adhesive layer.

19. The ostomy appliance of claim 1, wherein the fastener is attached to the bag by heat sealing.

20. The ostomy appliance of claim 1, wherein the fastener comprises the fastening layer and the fastening layer is laminated to the bag.

21. The ostomy appliance of claim 1, wherein the fastener is attached to the bag so as to form a flange.

22. The ostomy appliance of claim 1, wherein the fastener further comprises a gap filling material.

23. The ostomy appliance of claim 1, wherein the landing zone comprises: a non-tacky surface layer selected from the group consisting of a target surface layer and a contact responsive fastening layer; a layer of tacky adhesive; and a liner for protecting the tacky adhesive layer.

24. The ostomy appliance of claim 23, wherein the landing zone further comprises a tab for facilitating the separation of the liner from the tacky adhesive layer.

25. The ostomy appliance of claim 23, wherein the landing zone further comprises a slit liner for facilitating the separation of the liner from the tacky adhesive layer.

26. The ostomy appliance of claim 1, wherein the landing zone comprises the target surface layer, a layer of a skin barrier adhesive, and a liner for protecting the tacky adhesive layer.

27. The ostomy appliance of claim 23, wherein the landing zone further comprises a foam gap filling material.

28. The ostomy appliance of claim 23, wherein the landing zone further comprises a collar tape peripherally attached to the landing zone.

29. The ostomy appliance of claim 1, wherein the bag further comprising a drain.

30. The ostomy appliance of claim 1, wherein the bag further comprising an odor vent.

31. The ostomy appliance of claim 1, wherein the bag further comprising a comfort layer.

32. The ostomy appliance of claim 2, wherein the target surface is permanently attached to the bag and forms the fastener, and the fastening layer and adhesive layer are provided as the separable landing zone component.

33. The ostomy appliance of claim 2, wherein the surface of the bag surrounding the opening is a target surface and forms the fastener, and the fastening layer and adhesive layer are provided as the separable landing zone component.

34. An article, comprising:
   a bag with an opening for receiving material from an orifice, and
   a fastening system comprising (i) a landing zone having a non-tacky target surface layer and an adhesive layer for attaching the landing zone to the orifice area of a user and (ii) a fastener attached to the bag circumscribing the opening having a contact responsive non-tacky fastening layer that adheres to the non-tacky target surface layer, wherein the fastening layer demonstrates properties of: essentially no adhesion to paper; multiply repositionable against the non-tacky target surface; and a substantially constant low 90° peel strength of less than about 3 kN/m and a dynamic shear strength of greater than 2 $kN/m^2$ when in contact with the target surface, wherein the target surface is a different material than the fastening layer and has a solubility parameter that is sufficiently different from that of the polymer fastening layer to prevent blocking.

35. The article of claim 34, wherein the fastening layer comprises a polymer of from about 10 to about 50 weight percent of acrylonitrile and about 50 to about 90 weight percent of at least one of butadiene and isoprene.

36. A method of using an ostomy appliance having a non-tacky contact responsive fastener system comprising the steps of:
   a) providing a bag with an opening for receiving material from a stoma that has a fastening system comprising (i) a fastener attached to the bag circumscribing the opening and (ii) a landing zone, the fastening system having a non-tacky target surface layer, a contact responsive non-tacky fastening layer that adheres to the non-tacky target surface layer, and an adhesive layer;
   b) attaching the adhesive layer to the peristomal area of a user; and
   c) attaching the contact responsive non-tacky fastening layer to the non-tacky target surface layer.

* * * * *